US006846966B2

(12) United States Patent
Lumgair, Jr. et al.

(10) Patent No.: US 6,846,966 B2
(45) Date of Patent: Jan. 25, 2005

(54) METHOD AND APPARATUS FOR TREATING OXYGENATE-CONTAINING FEEDS AND THEIR USE IN CONVERSION OF OXYGENATES TO OLEFINS

(75) Inventors: David Ritchie Lumgair, Jr., Craddockville, VA (US); James H. Beech, Kingwood, TX (US); Michael Peter Nicoletti, Houston, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 31 days.

(21) Appl. No.: 10/304,328

(22) Filed: Nov. 26, 2002

(65) Prior Publication Data

US 2004/0102668 A1 May 27, 2004

(51) Int. Cl.[7] .................................................. C07C 1/00

(52) U.S. Cl. ..................................................... 585/639

(58) Field of Search ................................... 585/639, 640

(56) References Cited

U.S. PATENT DOCUMENTS

| 2,877,747 | A | 3/1959 | Happell ........................ 122/435 |
| 4,665,249 | A | 5/1987 | Mao et al. .................... 585/408 |
| 4,777,321 | A | 10/1988 | Harandi et al. ............. 585/640 |
| 4,814,535 | A | 3/1989 | Yurchak ....................... 585/408 |
| 4,814,536 | A | 3/1989 | Yurchak ....................... 585/408 |
| 4,826,662 | A | 5/1989 | Mao et al. .................... 422/190 |
| 5,028,400 | A | 7/1991 | Harandi et al. ............. 422/211 |
| 5,059,738 | A | 10/1991 | Beech, Jr. et al. .......... 585/469 |
| 6,121,504 | A | 9/2000 | Kuechler et al. ........... 585/640 |
| 6,166,282 | A | 12/2000 | Miller ......................... 585/637 |

FOREIGN PATENT DOCUMENTS

WO    WO 02/00579    1/2002    ........... C07C/11/02

*Primary Examiner*—Thuan D Dang

(57) ABSTRACT

A feed vaporization process and apparatus for oxygenate to olefin conversion is provided which uses a vapor-liquid disengaging drum to separate non-volatiles and/or partial non-volatiles from volatiles in the oxygenate feed and produce a vaporized effluent that is reduced in non-volatiles and/or partial non-volatiles while at the same time maintaining the effluent at optimal temperature and pressure as a feed for oxygenate to olefin conversion.

24 Claims, 1 Drawing Sheet

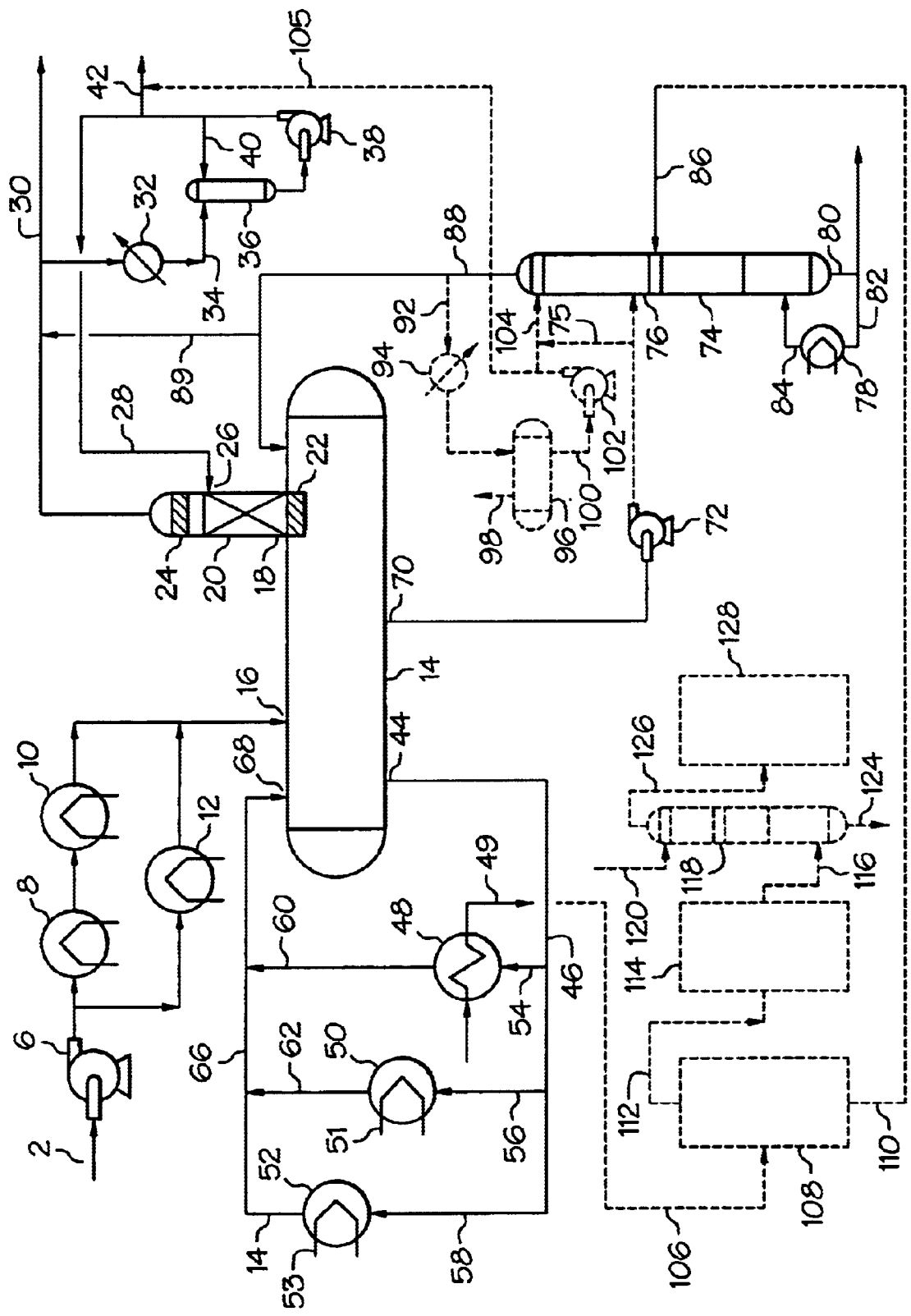

METHOD AND APPARATUS FOR TREATING OXYGENATE-CONTAINING FEEDS AND THEIR USE IN CONVERSION OF OXYGENATES TO OLEFINS

FIELD

The present invention relates to providing a feed for oxygenates to olefins conversion of reduced non-volatile contaminant content, while controlling functional temperature and pressure of the feed.

BACKGROUND

Light olefins, defined herein as ethylene, propylene, butylene and mixtures thereof, serve as feeds for the production of numerous important chemicals and polymers. Typically, light olefins are produced by cracking petroleum feeds. Because of the limited supply of competitive petroleum feeds, the opportunities to produce low cost light olefins from petroleum feeds are limited. Efforts to develop light olefin production technologies based on alternative feeds have increased.

An important type of alternate feed for the production of light olefins is oxygenate, such as, for example, alcohols, particularly methanol, ethanol, n-propanol, and iso-propanol, dimethyl ether, methyl ethyl ether, diethyl ether, dimethyl carbonate, and methyl formate. Many of these oxygenates may be produced by fermentation, or from synthesis gas derived from natural gas, petroleum liquids, carbonaceous materials, including coal, recycled plastics, municipal wastes, or any organic material. Because of the wide variety of sources, alcohol, alcohol derivatives, and other oxygenates have promise as an economical, non-petroleum source for light olefin production.

The catalysts used to promote the conversion of oxygenates to olefins are molecular sieve catalysts. Because ethylene and propylene are the most sought after products of such a reaction, research has focused on what catalysts are most selective to ethylene and/or propylene, and on methods for increasing the life and selectivity of the catalysts to ethylene and/or propylene.

Oxygenate-containing feeds may contain impurities which are deleterious to the catalysts employed in oxygenate to olefin conversion processes. Such impurities comprise non-volatile materials which have negligible vapor pressure at the conditions necessary to prepare feed for the oxygenates to olefin conversion process. Typically, these conditions include temperatures ranging from about 32° to about 500° F., and pressures ranging from about 20 psia to about 150 psia, say from about 50 to about 95 psia. A more detailed description of non-volatile materials is provided below with the description of the present invention.

The conversion of oxygenates to olefins (OTO) takes place at a relatively high temperature, generally higher than about 250° C., preferably higher than about 300° C. Because the conversion reaction is exothermic, the effluent typically has a higher temperature than the initial temperature in the reactor. Many methods and/or process schemes have been proposed to manage the heat of reaction generated from the oxygenate conversion reaction inside of the reactor in order to avoid temperature surges and hot spots, and thereby to reduce the rate of catalyst deactivation and reduce the production of undesirable products, such as methane, ethane, carbon monoxide and carbonaceous deposits or coke. These solutions involve heating the feed to proper temperature and pressure. However, this can lead to problems with the feed such as fouling. Although heavy hydrocarbons, metals and other non-volatile materials are not normally found in freshly produced oxygenated hydrocarbons, non-volatiles can be introduced during storage and handling of oxygenates, as well as during recycling of oxygenate streams to a reactor. Because of the relatively long residence times of catalyst in an oxygenates to olefins conversion reactor, even small amounts of non-volatile impurities/contaminants such as metals, salts and heavy hydrocarbons in the feed can accumulate on and thus poison the reactor's catalyst. These poisons interfere with the catalyst's function, reducing the efficiency of the catalyst and increasing the overall production costs. Given that non-volatiles in the feed at levels as low as one wppm can accumulate to 12000 wppm on the catalyst inventory, a compelling interest exists to provide feeds of extremely reduced non-volatiles content. Other processes have been taught that attempt to reduce the amount of catalyst poisons in the OTO reactor feed.

One of the processes that utilizes control of the OTO effluent temperature can be found in U.S. patent application Ser. No. 10/020,732, filed Oct. 30, 2001, entitled "Heat Recovery in an Olefin Production Process." In this application, which is incorporated herein by reference, a process for removing heat from an effluent stream while maintaining a temperature of the gas phase above the dew point is taught. By following this process, solid particles and some other contaminants may be separated from oxygenates. By removing these contaminants, the catalysts in the OTO reactor will perform better and last longer, thereby improving the reactor's efficiency and reducing production costs. Unfortunately, this process does not remove all catalyst poisons and further creates difficulties in maintaining the effluent at a proper temperature and pressure.

Improving the heating of an oxygenate-containing feed is described in U.S. Pat. No. 6,121,504, which is incorporated herein by reference. This patent teaches a series of heat exchangers to heat a feed using heat from the products of an OTO reactor. While this process efficiently heats the effluent, contaminants may still be present at the point where the effluent is fed into the OTO reactor, leading to the aforementioned problems downstream. Contaminants can be introduced not only from vapor feed streams, but from any liquid feed streams that may be used for reactor temperature control as well, e.g., where a reactor outlet temperature below that temperature obtained by equilibrium reactor heat balance for all vapor feed is desired. Accordingly, it is desirable that any liquid feed streams to the OTO reactor be very low in contaminant content, such as streams produced by condensing a clean vapor oxygenate stream, e.g., vaporized feed or recycle oxygenates streams that have been revaporized to remove non-volatiles.

It should thus be appreciated that a delicate balance exists between maintaining an oxygenate-containing feed for an OTO reactor at proper temperatures, while at the same time reducing or eliminating contaminants of such feed. Accordingly, it would be desirable to provide a process that effects substantial removal of contaminants that may poison an OTO reactor catalyst, while at the same time maintaining an effluent at a proper temperature and pressure.

SUMMARY

In one aspect, the present invention relates to a process for converting oxygenates to olefins which comprises: contacting a vaporized oxygenate-containing feed with a catalyst comprising a molecular sieve under conditions sufficient to provide an oxygenates to olefin effluent stream, and further comprising: providing said vaporized oxygenate-containing feed by: a) passing an initial oxygenate-containing feed having an initial heat content through at least one feed preheater under conditions sufficient to provide a feed of increased heat content; b) directing said feed of increased heat content to at least one vapor-liquid disengaging drum; c) providing conditions within said vapor-liquid disengaging drum sufficient to provide a vaporized oxygenate-containing stream and a liquid oxygenate-containing stream further comprising at least partial non-volatiles, wherein the boiling point of said oxygenates of said oxygenate-containing feed within said drum is controlled by varying the total pressure within the vapor-liquid disengaging drum so as to impart sufficient heat content to said vaporized oxygenate-containing stream, such that said contacting of the vaporized oxygenate-containing feed with said catalyst provides said effluent stream which comprises a superheated gas phase comprising olefins, typically prime olefins, defined herein as $C_2$ to $C_4$ olefins, e.g., ethylene, propylene and butenes, especially ethylene and propylene), unreacted oxygenate, and water at a temperature above that of said initial oxygenate-containing feed; d) heat exchanging said liquid oxygenate-containing stream by passage through at least one heat exchanger, external to said vapor-liquid disengaging drum, wherein heat is added to said liquid oxygenate-containing stream from said oxygenates to olefin effluent stream to provide a heat exchanged, at least partially vapor phase, oxygenate-containing stream; and e) directing said heat exchanged stream to said vapor-liquid disengaging drum. For present purposes, the term "at least partial non-volatiles" includes materials that include non-volatiles and/or partial non-volatiles. Partial non-volatiles are materials that are at least partially fractionatable, whilst non-volatiles are not fractionatable. The oxygenate-containing feed may contain alcohol, e.g., alcohol selected from methanol, ethanol, n-propanol and i-propanol and/or ether, e.g., ether selected from dimethyl ether, diethyl ether di-n-propyl ether and diisopropyl ether.

In one embodiment of this aspect of the invention, the at least one heat exchanger comprises a circulating partial vaporizer where said passage through the exchanger is induced by at least one of i) mechanically pumping said liquid oxygenate-containing stream through the heat exchanger and ii) thermosyphon circulation where the weight or density multiplied by height of the liquid oxygenate-containing stream minus total frictional losses being greater than the weight or density multiplied by height of the heat exchanged at least partially vapor phase, oxygenate-containing stream, drives said circulation.

In another embodiment, the at least one heat exchanger comprises a plurality of heat exchangers arranged in parallel.

In still another embodiment, at least one of said heat exchangers derives its heat from steam.

In yet another embodiment, at least one of said heat exchangers derives heat from water used to quench said oxygenates to olefin effluent stream. In still yet another embodiment, steam provides from about 10% to about 70% of said heat added to said liquid oxygenate-containing stream.

In still yet another embodiment, the heat exchanging is carried out to effect vaporization ranging from about 5 to about 95%, say, from about 20 to about 40%, of said liquid oxygenate-containing stream per pass through said circulating partial vaporizer.

In another embodiment, the liquid oxygenate-containing stream in the drum accumulates a desired proportion of the at least partial non-volatiles to provide an at least partial non-volatiles-rich, oxygenate-containing stream which is removable as blowdown.

In yet another embodiment, the non-volatiles-rich, oxygenate containing stream accumulates at least partial non-volatiles to a steady state level of from about 5 to about 100 times the level of non-volatiles in the initial oxygenate-containing feed, wherein liquid blowdown is removed from said vapor-liquid disengaging drum at a rate ranging from about 1% to about 20% by weight of said feed directed to said drum.

In yet another embodiment, the process of the invention comprises passing said blowdown as a feed to a condensate stripper to provide an at least partial non-volatiles-rich bottoms stream and an oxygenates-rich overhead.

In another embodiment, the oxygenates-rich overhead is recycled to the vapor-liquid disengaging drum.

In yet another embodiment, the oxygenates-rich overhead is recycled to a vapor-liquid disengaging drum and at least a portion of said blowdown is directed to a condensate stripper, e.g. as reflux.

In another embodiment, the oxygenates-rich overhead is directed to a vapor-liquid disengaging drum at least a portion of whose condensed liquid is directed to an oxygenates to olefin reactor as a liquid oxygenates-containing feed reduced in said at least partial non-volatiles.

In yet still another embodiment, the process of the invention further comprises: passing the vaporized oxygenate-containing stream from the vapor-liquid disengaging drum to a demister which provides a demisted oxygenate-containing stream as overhead, reduced in said at least partial non-volatiles. The demister reduces liquid droplet and associated entrained non-volatiles carry-over into the vapor effluent as a mist. Typically, the demister comprises a wire mesh screen sometimes referred to as a "crinkled wire mesh screen" or similar high surface to volume device to coalesce mist, placed in a vertical passage having a vapor superficial velocity less than about 16 ft/sec, preferably less than about 5 ft/sec and more preferably less than about 2 ft/sec. The demister can further comprise a wash column having a liquid oxygenates-containing stream as a wash liquid. Such wash liquid is typically substantially free of non-volatiles, i.e., having no more non-volatiles than the oxygenate feed. The wash rate is preferably less than about 10% by weight of the oxygenate vapor passing through the demister, more preferably less than about 3% by weight of the oxygenate passing through the demister. In one embodiment, a crinkled wire mesh screen is added to the top of the wash column above the point where the wash liquid is injected. Typically, a preheated methanol feed is directed to the wash column as liquid wash. In another embodiment a stream comprising oxygenates from the oxygenates to olefins product recovery system is directed to the washing column as liquid wash.

In another embodiment, the demister employs a washing column utilizing a reflux that comprises a liquid oxygenate-containing stream.

In one embodiment, at least some of the overhead from the demister is directed to a condenser to provide a liquid oxygenate-containing bottoms stream. The liquid oxygenate-containing bottoms stream, reduced in said at least partial non-volatiles, can be introduced as feed to an oxygenate to olefins reactor under conditions sufficient to provide an oxygenates to olefin effluent stream, alone or in conjunction with other liquid oxygenate-containing streams reduced in said at least partial non-volatiles produced by the process of the present invention.

In an alternative embodiment, at least a portion of the bottoms stream is used as wash liquid in the demister.

In still yet another embodiment, the at least one vapor-liquid disengaging drum is single vapor-liquid disengaging drum. The vapor-liquid disengaging drum is typically maintained at a pressure ranging from about 20 psia to about 150 psia, typically ranging from about 50 to about 95 psia.

In another embodiment, the oxygenate-containing feed comprises methanol.

In another aspect, the present invention relates to a process for vaporizing an oxygenate-containing feed which comprises: preheating a liquid oxygenate-containing feed containing at least partial non-volatiles and having an initial heat content, to provide a feed of increased heat content comprising a liquid phase and a vapor phase; passing said feed of increased heat content to at least one vapor-liquid disengaging drum to provide i) an overhead fraction comprising vaporized oxygenate-containing stream containing less than about 10 wt %, typically, less than about 5 wt %, say, less than about 1 wt %, e.g., less than about 0.1 wppm or even less than about 0.01 wppm, of non-volatiles in said feed plus an equilibrium amount of partial non-volatiles in the feed, and ii) a bottoms fraction comprising a liquid oxygenate-containing stream containing the at least partial non-volatiles derived from said feed which are not in said overhead fraction, and further wherein the boiling point in said vapor-liquid disengaging drum is controlled by varying the total pressure within the vapor-liquid disengaging drum; recovering said overhead fraction; directing said bottoms fraction containing liquid oxygenate-containing stream containing said at least partial non-volatiles through at least one heat exchanger external to said vapor-liquid disengaging drum, wherein heat is added to said liquid oxygenate-containing stream to provide a heat exchanged stream containing vapor phase oxygenate; and directing said heat-exchanged stream to said vapor-liquid disengaging drum.

In one embodiment of this aspect of the invention, the at least one heat exchanger comprises a of fluid through the exchanger by at least one of i) mechanically pumping said liquid oxygenate-containing stream through the heat exchanger and ii) thermosyphon circulation where the weight or density multiplied by height of the liquid oxygenate-containing stream minus total frictional losses being greater than the weight or density multiplied by height of the heat exchanged stream containing vapor phase oxygenate, drives said circulation.

In another embodiment of this aspect of the invention, the at least one heat exchanger comprises a plurality of heat exchangers arranged in parallel.

In still another embodiment of this aspect of the invention, heat is added to said liquid oxygenate-containing stream, said heat being taken from an oxygenates to olefin effluent stream.

In yet another embodiment of this aspect of the invention, at least one of said heat exchangers derives its heat from steam. Typically, said steam provides from about 10% to about 70% of said heat added to said liquid oxygenate-containing stream.

In still another embodiment of this aspect of the invention, the at least one of said heat exchangers derives heat from water used to quench an oxygenates to olefin effluent stream.

In still yet another embodiment of this aspect of the invention, the heat is added to an extent sufficient to effect vaporization ranging from about 5 to about 95%, say from about 20 to about 40%, per pass of circulating oxygenates in said liquid oxygenate-containing stream.

In another embodiment of this aspect of the invention, the liquid oxygenate-containing stream in said vapor-liquid disengaging drum accumulates a desired proportion of said at least partial non-volatiles to provide an at least partial non-volatiles-rich, oxygenate-containing stream which is removable as liquid blowdown.

In still another embodiment of this aspect of the invention, the at least partial non-volatiles-rich, oxygenate containing stream accumulates at least partial non-volatiles to a steady state level of from about 5 to about 100 times, say, from about 10 to about 50 times, the level of non-volatiles in said initial oxygenate-containing feed, wherein liquid blowdown is removed from the vapor-liquid disengaging drum at a rate ranging from about 1% to about 20%, say, from about 2% to about 10% by weight of total feed to said drum. In one embodiment, this blowdown can be passed as a feed to a condensate stripper to provide an at least partial non-volatiles-rich bottoms stream and an oxygenates-rich overhead. The oxygenates-rich overhead may be recycled to said vapor-liquid disengaging drum; and the at least partial non volatiles-rich bottoms stream can be removed from the condensate stripper. In another aspect, the oxygenates-rich overhead is recycled to a vapor-liquid disengaging drum and subsequently removed from the vapor-liquid drum as at least partially vaporized effluent; and at least part of the liquid blowdown is directed to the condensate stripper, e.g., as reflux. In still another aspect, at least some of the oxygenates-rich overhead is condensed and recycled as reflux to the condensate stripper.

In another aspect of this embodiment of the invention, the process further comprises: passing the vaporized oxygenate-containing stream from the vapor-liquid disengaging drum to a demister which provides a demisted oxygenate-containing stream as overhead, reduced in said at least partial non-volatiles. Typically, the demister comprises a wash column, and the wash column can utilize a liquid oxygenate-containing stream as wash liquid, which can be introduced at or near the top of the wash column.

In yet another aspect of this embodiment of the invention, the process further comprises directing at least some of the overhead from the demister to a condenser to provide a liquid oxygenate-containing bottoms stream reduced in the at least partial non-volatiles. This bottoms stream's reduced at least partial non-volatiles content makes it useful as an oxygenates to olefin reactor feed.

In another embodiment, at least a portion of the liquid oxygenates-containing bottoms stream is used as wash liquid in said demister. The process can further comprise condensing at least some of said oxygenates-rich overhead from the demister to a condenser and directing at least a portion of the resulting condensed stream as feed to an oxygenates to olefin reactor.

In still yet another embodiment, the process of the invention further comprises: directing an oxygenate-containing extract or a contaminated oxygenates stream from an olefins recovery process to an oxygenate to olefins reactor effluent quench column to provide oxygenate-containing condensate containing water; and stripping the oxygenate-containing condensate in a condensate stripper to provide an oxygenate-containing overhead from which water and at least partial non-volatiles are at least partially removed.

In still another embodiment, the process of the invention comprises: directing an oxygenate-containing extract from an olefins recovery process to a water stripper; stripping the oxygenate-containing extract to provide an oxygenate-containing overhead from which water and at least partial non-volatiles are removed.

In another aspect, the present invention relates to an apparatus for vaporizing an oxygenate-containing feed which comprises: a) an oxygenate-containing feed preheater which comprises an inlet for an oxygenate-containing feed of an initial heat content and an outlet for an oxygenate-containing feed having an increased heat content; b) an oxygenate vapor-liquid disengaging drum comprising an inlet for receiving the oxygenate-containing feed of increased heat content, a first outlet for removing an oxygenate-containing liquid phase, a second outlet for removing a blowdown fraction and a third outlet for removing an oxygenate-containing vapor phase; and c) a heat exchanger means for adding heat to said oxygenate-containing liquid phase comprising at least one heat exchanger, external to the vapor-liquid disengaging drum, comprising an inlet for the oxygenate-containing liquid phase having a first heat content and an outlet for an oxygenate-containing vapor phase which is connected to an inlet for the oxygenate vapor-liquid disengaging drum.

In another embodiment of this aspect of the invention, the heat exchanger means comprises a means for passing said oxygenate-containing liquid phase through said heat exchanger selected from i) a mechanical pump and ii) a thermosyphon.

In yet another embodiment of this aspect of the invention, the heat exchanger means comprises a plurality of said heat exchangers arranged in parallel.

In still another embodiment, at least some of the added heat is derived from an oxygenates to olefin reactor effluent.

In still yet another embodiment, at least some of the added heat is derived from steam.

In yet still another embodiment of this aspect of the invention, at least some of the added heat is derived from an oxygenates to olefin reactor effluent.

In another embodiment of this aspect of the invention, the apparatus further comprises: a demister associated with the oxygenate vapor outlet passage of the vapor-liquid disengaging drum to reduce liquid droplet and associated entrained non-volatiles carry-over into the vapor effluent as a mist, the demister comprising a lower inlet connected to said third outlet for removing an oxygenate-containing vapor phase, and an upper outlet for removing an oxygenate-containing demisted vapor phase.

In yet still another embodiment of the invention, the upper outlet is connected to a vapor feed inlet for an oxygenates to olefin reactor.

BRIEF DESCRIPTION OF THE DRAWINGS

The FIGURE depicts a schematic of certain embodiments of the present invention.

DETAILED DESCRIPTION OF THE INVENTION

Molecular Sieves and Catalysts Thereof for Use in OTO Conversion

Molecular sieves suited to use in the present invention for converting oxygenates to olefins have various chemical and physical, framework, characteristics. Molecular sieves have been well classified by the Structure Commission of the International Zeolite Association according to the rules of the IUPAC Commission on Zeolite Nomenclature. A framework-type describes the connectivity, topology, of the tetrahedrally coordinated atoms constituting the framework, and making an abstraction of the specific properties for those materials. Framework-type zeolite and zeolite-type molecular sieves for which a structure has been established, are assigned a three letter code and are described in the *Atlas of Zeolite Framework Types*, 5th edition, Elsevier, London, England (2001), which is herein fully incorporated by reference.

Non-limiting examples of these molecular sieves are the small pore molecular sieves of a framework-type selected from the group consisting of AEI, AFT, APC, ATN, ATT, ATV, AWW, BIK, CAS, CHA, CHI, DAC, DDR, EDI, ERI, GOO, KFI, LEV, LOV, LTA, MON, PAU, PHI, RHO, ROG, THO, and substituted forms thereof, the medium pore molecular sieves of a framework-type selected from the group consisting of AFO, AEL, EUO, HEU, FER, MEL, MFI, MTW, MTT, TON, and substituted forms thereof, and the large pore molecular sieves of a framework-type selected from the group consisting of EMT, FAU, and substituted forms thereof. Other molecular sieves have a framework-type selected from the group consisting of ANA, BEA, CFI, CLO, DON, GIS, LTL, MER, MOR, MWW and SOD. Non-limiting examples of the preferred molecular sieves, particularly for converting an oxygenate containing feedstock into olefin(s), include those having a framework-type selected from the group consisting of AEL, AFY, BEA, CHA, EDI, FAU, FER, GIS, LTA, LTL, MER, MFI, MOR, MTT, MWW, TAM and TON. In one preferred embodiment, the molecular sieve of the invention has an AEI topology or a CHA topology, or a combination thereof, most preferably a CHA topology.

Molecular sieve materials all have 3-dimensional, four-connected framework structure of corner-sharing $TO_4$ tetrahedra, where T is any tetrahedrally coordinated cation. These molecular sieves are typically described in terms of the size of the ring that defines a pore, where the size is based on the number of T atoms in the ring. Other framework-type characteristics include the arrangement of rings that form a cage, and when present, the dimension of channels, and the spaces between the cages. See van Bekkum, et al., *Introduction to Zeolite Science and Practice, Second Completely Revised and Expanded Edition*, Volume 137, pages 1–67, Elsevier Science, B. V., Amsterdam, Netherlands (2001).

The small, medium and large pore molecular sieves have from a 4-ring to a 12-ring or greater framework-type. In a preferred embodiment, the zeolitic molecular sieves have 8-, 10- or 12-ring structures or larger and an average pore size in the range of from about 3 Å to 15 Å. In the most preferred embodiment, the molecular sieves of the invention, preferably silicoaluminophosphate molecular sieves have 8-rings and an average pore size less than about 5 Å, preferably in the range of from 3 Å to about 5 Å, more preferably from 3 Å to about 4.5 Å, and most preferably from 3.5 Å to about 4.2 Å.

Molecular sieves, particularly zeolitic and zeolitic-type molecular sieves, preferably have a molecular framework of one, preferably two or more corner-sharing $[TO_4]$ tetrahedral units, more preferably, two or more $[SiO_4]$, $[AlO_4]$ and/or $[PO_4]$ tetrahedral units, and most preferably $[SiO_4]$, $[AlO_4]$ and $[PO_4]$ tetrahedral units. These silicon, aluminum, and phosphorous based molecular sieves and metal containing silicon, aluminum and phosphorous based molecular sieves have been described in detail in numerous publications including for example, U.S. Pat. No. 4,567,029 (MeAPO where Me is Mg, Mn, Zn, or Co), U.S. Pat. No. 4,440,871 (SAPO), European Patent Application EP-A-0 159 624 (ELAPSO where El is As, Be, B, Cr, Co, Ga, Ge, Fe, Li, Mg, Mn, Ti or Zn), U.S. Pat. No. 4,554,143 (FeAPO), U.S. Pat. Nos. 4,822,478, 4,683,217, 4,744,885 (FeAPSO), EP-A-0 158 975 and U.S. Pat. No. 4,935,216 (ZnAPSO, EP-A-0 161 489 (CoAPSO), EP-A-0 158 976 (ELAPO, where EL is Co, Fe, Mg, Mn, Ti or Zn), U.S. Pat. No. 4,310,440 (AlPO$_4$), EP-A-0 158 350 (SENAPSO), U.S. Pat. No. 4,973,460 (LiAPSO), U.S. Pat. No. 4,789,535 (LiAPO), U.S. Pat. No. 4,992,250 (GeAPSO), U.S. Pat. No. 4,888,167 (GeAPO), U.S. Pat. No. 5,057,295 (BAPSO), U.S. Pat. No. 4,738,837 (CrAPSO), U.S. Pat. Nos. 4,759,919, and 4,851,106 (CrAPO), U.S. Pat. Nos. 4,758,419, 4,882,038, 5,434,326 and 5,478,787 (MgAPSO), U.S. Pat. No. 4,554,143 (FeAPO), U.S. Pat. No. 4,894,213 (AsAPSO), U.S. Pat. No. 4,913,888 (AsAPO), U.S. Pat. Nos. 4,686,092, 4,846,956 and 4,793,833 (MnAPSO), U.S. Pat. Nos. 5,345,011 and 6,156,931 (MnAPO), U.S. Pat. No. 4,737,353 (BeAPSO), U.S. Pat. No. 4,940,570 (BeAPO), U.S. Pat. Nos. 4,801,309, 4,684,617 and 4,880,520 (TiAPSO), U.S. Pat. Nos. 4,500,651, 4,551,236 and 4,605,492 (TiAPO), U.S. Pat. No. 4,824,554, 4,744,970 (CoAPSO), U.S. Pat. No. 4,735,806 (GaAPSO) EP-A-0 293 937 (QAPSO, where Q is framework oxide unit [QO$_2$]), as well as U.S. Pat. Nos. 4,567,029, 4,686,093, 4,781,814, 4,793,984, 4,801,364, 4,853,197, 4,917,876, 4,952,384, 4,956,164, 4,956,165, 4,973,785, 5,241,093, 5,493,066 and 5,675,050, all of which are herein fully incorporated by reference.

Other molecular sieves include those described in EP-0 888 187 B1 (microporous crystalline metallophosphates, SAPO$_4$ (UIO-6)), U.S. Pat. No. 6,004,898 (molecular sieve and an alkaline earth metal), U.S. patent application Ser. No. 09/511,943 filed Feb. 24, 2000 (integrated hydrocarbon co-catalyst), PCT WO 01/64340 published Sep. 7, 2001 (thorium containing molecular sieve), and R. Szostak, *Handbook of Molecular Sieves*, Van Nostrand Reinhold, New York, N.Y. (1992), which are all herein fully incorporated by reference.

The more preferred silicon, aluminum and/or phosphorous containing molecular sieves, and aluminum, phosphorous, and optionally silicon, containing molecular sieves include aluminophosphate (ALPO) molecular sieves and silicoaluminophosphate (SAPO) molecular sieves and substituted, preferably metal substituted, ALPO and SAPO molecular sieves. The most preferred molecular sieves are SAPO molecular sieves, and metal substituted SAPO molecular sieves. In an embodiment, the metal is an alkali metal of Group IA of the Periodic Table of Elements, an alkaline earth metal of Group IIA of the Periodic Table of Elements, a rare earth metal of Group IIIB, including the Lanthanides: lanthanum, cerium, praseodymium, neodymium, samarium, europium, gadolinium, terbium, dysprosium, holmium, erbium, thulium, ytterbium and lutetium; and scandium or yttrium of the Periodic Table of Elements, a transition metal of Groups IVB, VB, VIB, VIIB, VIIIB, and IB of the Periodic Table of Elements, or mixtures of any of these metal species. In one preferred embodiment, the metal is selected from the group consisting of Co, Cr, Cu, Fe, Ga, Ge, Mg, Mn, Ni, Sn, Ti, Zn and Zr, and mixtures thereof. In another preferred embodiment, these metal atoms discussed above are inserted into the framework of a molecular sieve through a tetrahedral unit, such as [MeO$_2$], and carry a net charge depending on the valence state of the metal substituent. For example, in one embodiment, when the metal substituent has a valence state of +2, +3, +4, +5, or +6, the net charge of the tetrahedral unit is between −2 and +2.

In one embodiment, the molecular sieve, as described in many of the U.S. Patents mentioned above, is represented by the empirical formula, on an anhydrous basis:

mR:(M$_x$Al$_y$P$_z$)O$_2$ wherein R represents at least one templating agent, preferably an organic templating agent; m is the number of moles of R per mole of (M$_x$Al$_y$P$_z$)O$_2$ and m has a value from 0 to 1, preferably 0 to 0.5, and most preferably from 0 to 0.3; x, y, and z represent the mole fraction of Al, P and M as tetrahedral oxides, where M is a metal selected from one of Group IA, IIA, IB, IIIB, IVB, VB, VIB, VIIB, VIIIB and Lanthanide's of the Periodic Table of Elements, preferably M is selected from one of the group consisting of Co, Cr, Cu, Fe, Ga, Ge, Mg, Mn, Ni, Sn, Ti, Zn and Zr. In an embodiment, m is greater than or equal to 0.2, and x, y and z are greater than or equal to 0.01.

In another embodiment, m is greater than 0.1 to about 1, x is greater than 0 to about 0.25, y is in the range of from 0.4 to 0.5, and z is in the range of from 0.25 to 0.5, more preferably m is from 0.15 to 0.7, x is from 0.01 to 0.2, y is from 0.4 to 0.5, and z is from 0.3 to 0.5.

Non-limiting examples of SAPO and ALPO molecular sieves of the invention include one or a combination of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44 (U.S. Pat. No. 6,162,415), SAPO-47, SAPO-56, ALPO-5, ALPO-11, ALPO-18, ALPO-31, ALPO-34, ALPO-36, ALPO-37, ALPO-46, and metal containing molecular sieves thereof. The more preferred zeolite-type molecular sieves include one or a combination of SAPO-18, SAPO-34, SAPO-35, SAPO-44, SAPO-56, ALPO-18 and ALPO-34, even more preferably one or a combination of SAPO-18, SAPO-34, ALPO-34 and ALPO-18, and metal containing molecular sieves thereof, and most preferably one or a combination of SAPO-34 and ALPO-18, and metal containing molecular sieves thereof.

In an embodiment, the molecular sieve is an intergrowth material having two or more distinct phases of crystalline structures within one molecular sieve composition. In particular, intergrowth molecular sieves are described in the U.S. patent application Ser. No. 09/924,016 filed Aug. 7, 2001 and PCT WO 98/15496 published Apr. 16, 1998, both of which are herein fully incorporated by reference. In another embodiment, the molecular sieve comprises at least one intergrown phase of AEI and CHA framework-types. For example, SAPO-18, ALPO-18 and RUW-18 have an AEI framework-type, and SAPO-34 has a CHA framework-type.

Molecular Sieve Synthesis

The synthesis of molecular sieves is described in many of the references discussed above. Generally, molecular sieves are synthesized by the hydrothermal crystallization of one or more of a source of aluminum, a source of phosphorous, a source of silicon, a templating agent, and a metal containing compound. Typically, a combination of sources of silicon, aluminum and phosphorous, optionally with one or more templating agents and/or one or more metal containing compounds are placed in a sealed pressure vessel, optionally lined with an inert plastic such as polytetrafluoroethylene, and heated, under a crystallization pressure and temperature, until a crystalline material is formed, and then recovered by filtration, centrifugation and/or decanting.

In a preferred embodiment the molecular sieves are synthesized by forming a reaction product of a source of silicon, a source of aluminum, a source of phosphorous, an organic templating agent, preferably a nitrogen containing organic templating agent, and one or more polymeric bases. This particularly preferred embodiment results in the synthesis of a silicoaluminophosphate crystalline material that is then isolated by filtration, centrifugation and/or decanting.

Non-limiting examples of silicon sources include a silicates, fumed silica, for example, Aerosil-200 available from Degussa Inc., New York, N.Y., and CAB-O-SIL M-5, silicon compounds such as tetraalkyl orthosilicates, for example, tetramethyl orthosilicate (TMOS) and tetraethylorthosilicate (TEOS), colloidal silicas or aqueous suspensions thereof, for example Ludox-HS-40 sol available from E.I. du Pont de Nemours, Wilmington, Del., silicic acid, alkali-metal silicate, or any combination thereof. The preferred source of silicon is a silica sol.

Non-limiting examples of aluminum sources include aluminum-containing compositions such as aluminum alkoxides, for example aluminum isopropoxide, aluminum phosphate, aluminum hydroxide, sodium aluminate, pseudo-boehmite, gibbsite and aluminum trichloride, or any combinations thereof. A preferred source of aluminum is pseudo-boehmite, particularly when producing a silicoaluminophosphate molecular sieve.

Non-limiting examples of phosphorous sources, which may also include aluminum-containing phosphorous compositions, include phosphorous-containing, inorganic or organic, compositions such as phosphoric acid, organic phosphates such as triethyl phosphate, and crystalline or amorphous aluminophosphates such as $ALPO_4$, phosphorous salts, or combinations thereof. The preferred source of phosphorous is phosphoric acid, particularly when producing a silicoaluminophosphate.

Templating agents are generally compounds that contain elements of Group VA of the Periodic Table of Elements, particularly nitrogen, phosphorus, arsenic and antimony, more preferably nitrogen or phosphorous, and most preferably nitrogen. Typical templating agents of Group VA of the Periodic Table of elements also contain at least one alkyl or aryl group, preferably an alkyl or aryl group having from 1 to 10 carbon atoms, and more preferably from 1 to 8 carbon atoms. The preferred templating agents are nitrogen-containing compounds such as amines and quaternary ammonium compounds.

The quaternary ammonium compounds, in one embodiment, are represented by the general formula $R_4N^+$, where each R is hydrogen or a hydrocarbyl or substituted hydrocarbyl group, preferably an alkyl group or an aryl group having from 1 to 10 carbon atoms. In one embodiment, the templating agents include a combination of one or more quaternary ammonium compound(s) and one or more of a mono-, di- or tri-amine.

Non-limiting examples of templating agents include tetraalkyl ammonium compounds including salts thereof such as tetramethyl ammonium compounds including salts thereof, tetraethyl ammonium compounds including salts thereof, tetrapropyl ammonium including salts thereof, and tetrabutylammonium including salts thereof, cyclohexylamine, morpholine, di-n-propylamine (DPA), tripropylamine, triethylamine (TEA), triethanolamine, piperidine, cyclohexylamine, 2-methylpyridine, N,N-dimethylbenzylamine, N,N-diethylethanolamine, dicyclohexylamine, N,N-dimethylethanolamine, choline, N,N'-dimethylpiperazine, 1,4-diazabicyclo(2,2,2)octane, N',N',N,N-tetramethyl(1,6)hexanediamine, N-methyldiethanolamine, N-methyl-ethanolamine, N-methyl piperidine, 3-methyl-piperidine, N-methylcyclohexylamine, 3-methylpyridine, 4-methylpyridine, quinuclidine, N,N'-dimethyl-1,4-diazabicyclo(2,2,2)octane ion; di-n-butylamine, neopentylamine, di-n-pentylamine, isopropylamine, t-butylamine, ethylenediamine, pyrrolidine, and 2-imidazolidone.

The preferred templating agent or template is a tetraethylammonium compound, such as tetraethyl ammonium hydroxide (TEAOH), tetraethyl ammonium phosphate, tetraethyl ammonium fluoride, tetraethyl ammonium bromide, tetraethyl ammonium chloride and tetraethyl ammonium acetate. The most preferred templating agent is tetraethyl ammonium hydroxide and salts thereof, particularly when producing a silicoaluminophosphate molecular sieve. In one embodiment, a combination of two or more of any of the above templating agents is used in combination with one or more of a silicon-, aluminum-, and phosphorous-source, and a polymeric base.

Polymeric bases, especially polymeric bases that are soluble or non-ionic, useful in the invention, are those having a pH sufficient to control the pH desired for synthesizing a given molecular sieve, especially a SAPO molecular sieve. In a preferred embodiment, the polymeric base is soluble or the polymeric base is non-ionic, preferably the polymeric base is a non-ionic and soluble polymeric base, and most preferably the polymeric base is a polymeric imine. In one embodiment, the polymeric base of the invention has a pH in an aqueous solution, preferably water, from greater than 7 to about 14, more preferably from about 8 to about 14, most preferably from about 9 to 14.

In another embodiment, the non-volatile polymeric base is represented by the formula: $(R-NH)_x$, where (R—NH) is a polymeric or monomeric unit where R contains from 1 to 20 carbon atoms, preferably from 1 to 10 carbon atoms, more preferably from 1 to 6 carbon atoms, and most preferably from 1 to 4 carbon atoms; x is an integer from 1 to 500,000. In one embodiment, R is a linear, branched, or cyclic polymer, monomeric, chain, preferably a linear polymer chain having from 1 to 20 carbon atoms.

In another embodiment, the polymeric base is a water miscible polymeric base, preferably in an aqueous solution. In yet another embodiment, the polymeric base is a polyethylenimine that is represented by the following general formula:

$(-NHCH_2CH_2-)_m[-N(CH_2CH_2NH_2)CH_2CH_2-]_n$), wherein m is from 10 to 20,000, and n is from 0 to 2,000, preferably from 1 to 2000.

In another embodiment, the polymeric base of the invention has a average molecular weight from about 500 to about 1,000,000, preferably from about 2,000 to about 800,000, more preferably from about 10,000 to about 750,000, and most preferably from about 50,000 to about 750,000.

In another embodiment, the mole ratio of the monomeric unit of the polymeric base of the invention, containing one basic group, to the templating agent(s) is less than 20, preferably less than 12, more preferably less than 10, even more preferably less than 8, still even more preferably less than 5, and most preferably less than 4.

Non-limiting examples of polymer bases include: epichlorohydrin modified polyethylenimine, ethoxylated polyethylenimine, polypropylenimine diamine dendrimers (DAB-Am-n), poly(allylamine)$[CH_2CH(CH_2NH_2)]_n$, poly (1,2-dihydro-2,2,4-trimethylquinoline), and poly (dimethylamine-co-epichlorohydrin-co-ethylenediamine).

In another embodiment the invention is directed to a method for synthesizing a molecular sieve utilizing a templating agent, preferably an organic templating agent such as an organic amine, an ammonium salt and/or an ammonium hydroxide, in combination with a polymeric base such as polyethylenimine.

In a typical synthesis of the molecular sieve, the phosphorous-, aluminum-, and/or silicon-containing components are mixed, preferably while stirring and/or agitation and/or seeding with a crystalline material, optionally with an alkali metal, in a solvent such as water, and one or more templating agents and a polymeric base, to form a synthesis mixture that is then heated under crystallization conditions of pressure and temperature as described in U.S. Pat. Nos. 4,440,871, 4,861,743, 5,096,684, and 5,126,308, which are all herein fully incorporated by reference. The polymeric base is combined with the at least one templating agent, and one or more of the aluminum source, phosphorous source, and silicon source, in any order, for example, simultaneously with one or more of the sources, premixed with one or more of the sources and/or templating agent, after combining the sources and the templating agent, and the like.

Generally, the synthesis mixture described above is sealed in a vessel and heated, preferably under autogenous pressure, to a temperature in the range of from about 80° C. to about 250° C., preferably from about 100° C. to about 250° C., more preferably from about 125° C. to about 225° C., even more preferably from about 150° C. to about 180° C. In another embodiment, the hydrothermal crystallization temperature is less than 225° C., preferably less than 200° C. to about 80° C., and more preferably less than 195° C. to about 100° C.

In yet another embodiment, the crystallization temperature is increased gradually or stepwise during synthesis, preferably the crystallization temperature is maintained constant, for a period of time effective to form a crystalline product. The time required to form the crystalline product is typically from immediately up to several weeks, the duration of which is usually dependent on the temperature; the higher the temperature the shorter the duration. In one embodiment, the crystalline product is formed under heating from about 30 minutes to around 2 weeks, preferably from about 45 minutes to about 240 hours, and more preferably from about 1 hour to about 120 hours.

In one embodiment, the synthesis of a molecular sieve is aided by seeds from another or the same framework type molecular sieve.

The hydrothermal crystallization is carried out with or without agitation or stirring, for example stirring or tumbling. The stirring or agitation during the crystallization period may be continuous or intermittent, preferably continuous agitation. Typically, the crystalline molecular sieve product is formed, usually in a slurry state, and is recovered by any standard technique well known in the art, for example centrifugation or filtration. The isolated or separated crystalline product, in an embodiment, is washed, typically, using a liquid such as water, from one to many times. The washed crystalline product is then optionally dried, preferably in air.

One method for crystallization involves subjecting an aqueous reaction mixture containing an excess amount of a templating agent and polymeric base, subjecting the mixture to crystallization under hydrothermal conditions, establishing an equilibrium between molecular sieve formation and dissolution, and then, removing some of the excess templating agent and/or organic base to inhibit dissolution of the molecular sieve. See for example U.S. Pat. No. 5,296,208, which is herein fully incorporated by reference.

Another method of crystallization is directed to not stirring a reaction mixture, for example a reaction mixture containing at a minimum, a silicon-, an aluminum-, and/or a phosphorous-composition, with a templating agent and a polymeric base, for a period of time during crystallization. See PCT WO 01/47810 published Jul. 5, 2001, which is herein fully incorporated by reference.

Other methods for synthesizing molecular sieves or modifying molecular sieves are described in U.S. Pat. No. 5,879,655 (controlling the ratio of the templating agent to phosphorous), U.S. Pat. No. 6,005,155 (use of a modifier without a salt), U.S. Pat. No. 5,475,182 (acid extraction), U.S. Pat. No. 5,962,762 (treatment with transition metal), U.S. Pat. Nos. 5,925,586 and 6,153,552 (phosphorous modified), U.S. Pat. No. 5,925,800 (monolith supported); U.S. Pat. No. 5,932,512 (fluorine treated), U.S. Pat. No. 6,046,373 (electromagnetic wave treated or modified), U.S. Pat. No. 6,051,746 (polynuclear aromatic modifier), U.S. Pat. No. 6,225,254 (heating template), PCT WO 01/36329 published May 25, 2001 (surfactant synthesis), PCT WO 01/25151 published Apr. 12, 2001 (staged acid addition), PCT WO 01/60746 published Aug. 23, 2001 (silicon oil), U.S. patent application Ser. No. 09/929,949 filed Aug. 15, 2001 (cooling molecular sieve), U.S. patent application Ser. No. 09/615,526 filed Jul. 13, 2000 (metal impregnation including copper), U.S. patent application Ser. No. 09/672,469 filed Sep. 28, 2000 (conductive microfilter), and U.S. patent application Ser. No. 09/754,812 filed Jan. 4, 2001 (freeze drying the molecular sieve), which are all herein fully incorporated by reference.

In one preferred embodiment, when a templating agent is used in the synthesis of a molecular sieve, it is preferred that the templating agent is substantially, preferably completely, removed after crystallization by numerous well known techniques, for example, heat treatments such as calcination. Calcination involves contacting the molecular sieve containing the templating agent with a gas, preferably containing oxygen, at any desired concentration at an elevated temperature sufficient to either partially or completely decompose and oxidize the templating agent.

Molecular sieves have either a high silicon (Si) to aluminum (Al) ratio or a low silicon to aluminum ratio, however, a low Si/Al ratio is preferred for SAPO synthesis. In one embodiment, the molecular sieve has a Si/Al ratio less than 0.65, preferably less than 0.40, more preferably less than 0.32, and most preferably less than 0.20. In another embodiment the molecular sieve has a Si/Al ratio in the range of from about 0.65 to about 0.10, preferably from about 0.40 to about 0.10, more preferably from about 0.32 to about 0.10, and more preferably from about 0.32 to about 0.15.

The pH of a reaction mixture containing at a minimum a silicon-, aluminum-, and/or phosphorous-composition, a templating agent, and a polymeric base should be in the range of from 2 to 10, preferably in the range of from 4 to 9, and most preferably in the range of from 5 to 8. The pH can be controlled by the addition of basic or acidic compounds as necessary to maintain the pH during the synthesis in the preferred range of from 4 to 9. In another embodiment, the templating agent and/or polymeric base is added to the reaction mixture of the silicon source and phosphorous source such that the pH of the reaction mixture does not exceed 10.

In one embodiment, the molecular sieves of the invention are combined with one or more other molecular sieves. In another embodiment, the preferred silicoaluminophosphate or aluminophosphate molecular sieves, or a combination thereof, are combined with one more of the following non-limiting examples of molecular sieves described in the following: Beta (U.S. Pat. No. 3,308,069), ZSM-5 (U.S. Pat. Nos. 3,702,886, 4,797,267 and 5,783,321), ZSM-11 (U.S. Pat. No. 3,709,979), ZSM-12 (U.S. Pat. No. 3,832,449), ZSM-12 and ZSM-38 (U.S. Pat. No. 3,948,758), ZSM-22 (U.S. Pat. No. 5,336,478), ZSM-23 (U.S. Pat. No. 4,076,842), ZSM-34 (U.S. Pat. No. 4,086,186), ZSM-35 (U.S. Pat. No. 4,016,245, ZSM-48 (U.S. Pat. No. 4,397,827), ZSM-58 (U.S. Pat. No. 4,698,217), MCM-1 (U.S. Pat. No. 4,639,358), MCM-2 (U.S. Pat. No. 4,673,559), MCM-3 (U.S. Pat. No. 4,632,811), MCM-4 (U.S. Pat. No. 4,664,897), MCM-5

(U.S. Pat. No. 4,639,357), MCM-9 (U.S. Pat. No. 4,880,611), MCM-10 (U.S. Pat. No. 4,623,527), MCM-14 (U.S. Pat. No. 4,619,818), MCM-22 (U.S. Pat. No. 4,954,325), MCM-41 (U.S. Pat. No. 5,098,684), M-41S (U.S. Pat. No. 5,102,643), MCM-48 (U.S. Pat. No. 5,198,203), MCM-49 (U.S. Pat. No. 5,236,575), MCM-56 (U.S. Pat. No. 5,362,697), ALPO-11 (U.S. Pat. No. 4,310,440), titanium aluminosilicates (TASO), TASO-45 (EP-A-0 229,-295), boron silicates (U.S. Pat. No. 4,254,297), titanium aluminophosphates (TAPO) (U.S. Pat. No. 4,500,651), mixtures of ZSM-5 and ZSM-11 (U.S. Pat. No. 4,229,424), ECR-18 (U.S. Pat. No. 5,278,345), SAPO-34 bound ALPO-5 (U.S. Pat. No. 5,972,203), PCT WO 98/57743 published Dec. 23, 1988 (molecular sieve and Fischer-Tropsch), U.S. Pat. No. 6,300,535 (MFI-bound zeolites), and mesoporous molecular sieves (U.S. Pat. Nos. 6,284,696, 5,098,684, 5,102,643 and 5,108,725), which are all herein fully incorporated by reference.

Method for Making Molecular Sieve Catalyst Compositions

Once the molecular sieve is synthesized, depending on the requirements of the particular conversion process, the molecular sieve is then formulated into a molecular sieve catalyst composition, particularly for commercial use. The molecular sieves synthesized above are made or formulated into catalysts by combining the synthesized molecular sieves with a binder and/or a matrix material to form a molecular sieve catalyst composition or a formulated molecular sieve catalyst composition. This formulated molecular sieve catalyst composition is formed into useful shape and sized particles by well-known techniques such as spray drying, pelletizing, extrusion, and the like.

There are many different binders that are useful in forming the molecular sieve catalyst composition. Non-limiting examples of binders that are useful alone or in combination include various types of hydrated alumina, silicas, and/or other inorganic oxide sol. One preferred alumina containing sol is aluminum chlorhydrol. The inorganic oxide sol acts like glue binding the synthesized molecular sieves and other materials such as the matrix together, particularly after thermal treatment. Upon heating, the inorganic oxide sol, preferably having a low viscosity, is converted into an inorganic oxide matrix component. For example, an alumina sol will convert to an aluminum oxide matrix following heat treatment.

Aluminum chlorhydrol, a hydroxylated aluminum based sol containing a chloride counter ion, has the general formula of $Al_mO_n(OH)_oCl_p \cdot x(H_2O)$ wherein m is 1 to 20, n is 1 to 8, o is 5 to 40, p is 2 to 15, and x is 0 to 30. In one embodiment, the binder is $Al_{13}O_4(OH)_{24}Cl_7 \cdot 12(H_2O)$ as is described in G. M. Wolterman, et al., Stud. Surf. Sci. and Catal., 76, pages 105–144 (1993), which is herein incorporated by reference. In another embodiment, one or more binders are combined with one or more other non-limiting examples of alumina materials such as aluminum oxyhydroxide, γ-alumina, boehmite, diaspore, and transitional aluminas such as α-alumina, β-alumina, γ-alumina, δ-alumina, ε-alumina, κ-alumina, and ρ-alumina, aluminum trihydroxide, such as gibbsite, bayerite, nordstrandite, doyelite, and mixtures thereof.

In another embodiment, the binders are alumina sols, predominantly comprising aluminum oxide, optionally including some silicon. In yet another embodiment, the binders are peptized alumina made by treating alumina hydrates such as pseudobohemite, with an acid, preferably an acid that does not contain a halogen, to prepare sols or aluminum ion solutions. Non-limiting examples of commercially available colloidal alumina sols include Nalco 8676 available from Nalco Chemical Co., Naperville, Ill., and Nyacol available from The PQ Corporation, Valley Forge, Pa.

The molecular sieve synthesized above, in a preferred embodiment, is combined with one or more matrix material(s). Matrix materials are typically effective in reducing overall catalyst cost, act as thermal sinks assisting in shielding heat from the catalyst composition for example during regeneration, densifying the catalyst composition, increasing catalyst strength such as crush strength and attrition resistance, and to control the rate of conversion in a particular process.

Non-limiting examples of matrix materials include one or more of: rare earth metals, metal oxides including titania, zirconia, magnesia, thoria, beryllia, quartz, silica or sols, and mixtures thereof, for example silica-magnesia, silica-zirconia, silica-titania, silica-alumina and silica-alumina-thoria. In an embodiment, matrix materials are natural clays such as those from the families of montmorillonite and kaolin. These natural clays include subbentonites and those kaolins known as, for example, Dixie, McNamee, Georgia and Florida clays. Non-limiting examples of other matrix materials include: haloysite, kaolinite, dickite, nacrite, or anauxite. In one embodiment, the matrix material, preferably any of the clays, are subjected to well known modification processes such as calcination and/or acid treatment and/or chemical treatment.

In one preferred embodiment, the matrix material is a clay or a clay-type composition, preferably the clay or clay-type composition having a low iron or titania content, and most preferably the matrix material is kaolin. Kaolin has been found to form a pumpable, high solid content slurry, it has a low fresh surface area, and it packs together easily due to its platelet structure. A preferred average particle size of the matrix material, most preferably kaolin, is from about 0.1 $\mu$m to about 0.6 $\mu$m with a $d_{90}$ particle size distribution of less than about 1 $\mu$m.

In one embodiment, the binder, the molecular sieve and the matrix material are combined in the presence of a liquid to form a molecular sieve catalyst composition, where the amount of binder is from about 2% by weight to about 30% by weight, preferably from about 5% by weight to about 20% by weight, and more preferably from about 7% by weight to about 15% by weight, based on the total weight of the binder, the molecular sieve and matrix material, excluding the liquid (after calcination).

In another embodiment, the weight ratio of the binder to the matrix material used in the formation of the molecular sieve catalyst composition is from 0:1 to 1:15, preferably 1:15 to 1:5, more preferably 1:10 to 1:4, and most preferably 1:6 to 1:5. It has been found that a higher sieve content, lower matrix content, increases the molecular sieve catalyst composition performance, however, lower sieve content, higher matrix material, improves the attrition resistance of the composition.

Upon combining the molecular sieve and the matrix material, optionally with a binder, in a liquid to form a slurry, mixing, preferably rigorous mixing is needed to produce a substantially homogeneous mixture containing the molecular sieve. Non-limiting examples of suitable liquids include one or a combination of water, alcohol, ketones, aldehydes, and/or esters. The most preferred liquid is water. In one embodiment, the slurry is colloid-milled for a period of time sufficient to produce the desired slurry texture, sub-particle size, and/or sub-particle size distribution.

The molecular sieve and matrix material, and the optional binder, are in the same or different liquid, and are combined in any order, together, simultaneously, sequentially, or a combination thereof. In the preferred embodiment, the same liquid, preferably water is used. The molecular sieve, matrix material, and optional binder, are combined in a liquid as solids, substantially dry or in a dried form, or as slurries, together or separately. If solids are added together as dry or substantially dried solids, it is preferable to add a limited and/or controlled amount of liquid.

In one embodiment, the slurry of the molecular sieve, binder and matrix materials is mixed or milled to achieve a sufficiently uniform slurry of sub-particles of the molecular sieve catalyst composition that is then fed to a forming unit that produces the molecular sieve catalyst composition. In a preferred embodiment, the forming unit is spray dryer. Typically, the forming unit is maintained at a temperature sufficient to remove most of the liquid from the slurry, and from the resulting molecular sieve catalyst composition. The resulting catalyst composition when formed in this way takes the form of microspheres.

When a spray drier is used as the forming unit, typically, the slurry of the molecular sieve and matrix material, and optionally a binder, is co-fed to the spray drying volume with a drying gas with an average inlet temperature ranging from 200° C. to 550° C., and a combined outlet temperature ranging from 100° C. to about 225° C. In an embodiment, the average diameter of the spray dried formed catalyst composition is from about 40 μm to about 300 μm, preferably from about 50 μm to about 250 μm, more preferably from about 50 μm to about 200 μm, and most preferably from about 65 μm to about 90 μm.

During spray drying, the slurry is passed through a nozzle distributing the slurry into small droplets, resembling an aerosol spray into a drying chamber. Atomization is achieved by forcing the slurry through a single nozzle or multiple nozzles with a pressure drop in the range of from 100 psia to 1000 psia (690 kPaa to 6895 kPaa). In another embodiment, the slurry is co-fed through a single nozzle or multiple nozzles along with an atomization fluid such as air, steam, flue gas, or any other suitable gas.

In yet another embodiment, the slurry described above is directed to the perimeter of a spinning wheel that distributes the slurry into small droplets, the size of which is controlled by many factors including slurry viscosity, surface tension, flow rate, pressure, and temperature of the slurry, the shape and dimension of the nozzle(s), or the spinning rate of the wheel. These droplets are then dried in a co-current or counter-current flow of air passing through a spray drier to form a substantially dried or dried molecular sieve catalyst composition, more specifically a molecular sieve in powder form.

Generally, the size of the powder is controlled to some extent by the solids content of the slurry. However, control of the size of the catalyst composition and its spherical characteristics are controllable by varying the slurry feed properties and conditions of atomization.

Other methods for forming a molecular sieve catalyst composition are described in U.S. patent application Ser. No. 09/617,714 filed Jul. 17, 2000 (spray drying using a recycled molecular sieve catalyst composition), which is herein incorporated by reference.

In another embodiment, the formulated molecular sieve catalyst composition contains from about 1% to about 99%, more preferably from about 5% to about 90%, and most preferably from about 10% to about 80%, by weight of the molecular sieve based on the total weight of the molecular sieve catalyst composition.

In another embodiment, the weight percent of binder in or on the spray dried molecular sieve catalyst composition based on the total weight of the binder, molecular sieve, and matrix material is from about 2% by weight to about 30% by weight, preferably from about 5% by weight to about 20% by weight, and more preferably from about 7% by weight to about 15% by weight.

Once the molecular sieve catalyst composition is formed in a substantially dry or dried state, to further harden and/or activate the formed catalyst composition, a heat treatment such as calcination, at an elevated temperature is usually performed. A conventional calcination environment is air that typically includes a small amount of water vapor. Typical calcination temperatures are in the range from about 400° C. to about 1,000° C., preferably from about 500° C. to about 800° C., and most preferably from about 550° C. to about 700° C., preferably in a calcination environment such as air, nitrogen, helium, flue gas (combustion product lean in oxygen), or any combination thereof.

In one embodiment, calcination of the formulated molecular sieve catalyst composition is carried out in any number of well known devices including rotary calciners, fluid bed calciners, batch ovens, and the like. Calcination time is typically dependent on the degree of hardening of the molecular sieve catalyst composition and the temperature ranges from about 15 minutes to about 2 hours.

In a preferred embodiment, the molecular sieve catalyst composition is heated in nitrogen at a temperature of from about 600° C. to about 700° C. Heating is carried out for a period of time typically from 30 minutes to 15 hours, preferably from 1 hour to about 10 hours, more preferably from about 1 hour to about 5 hours, and most preferably from about 2 hours to about 4 hours.

Other methods for activating a molecular sieve catalyst composition, in particular where the molecular sieve is a reaction product of the combination of a silicon-, phosphorous-, and aluminum-sources, a templating agent, and a polymeric base, more particularly a silicoaluminophosphate catalyst composition (SAPO) are described in, for example, U.S. Pat. No. 5,185,310 (heating molecular sieve of gel alumina and water to 450° C.), PCT WO 00/75072 published Dec. 14, 2000 (heating to leave an amount of template), and U.S. application Ser. No. 09/558,774 filed Apr. 26, 2000 (rejuvenation of molecular sieve), which are all herein fully incorporated by reference.

Aluminum chlorhydrol, a hydroxylated aluminum based sol containing a chloride counter ion, has the general formula of $Al_mO_n(OH)_oCl_p \cdot x(H_2O)$ wherein m is 1 to 20, n is 1 to 8, o is 5 to 40, p is 2 to 15, and x is 0 to 30. In one embodiment, the binder is $Al_{13}O_4(OH)_{24}Cl_7 \cdot 12(H_2O)$ as is described in G. M. Wolterman, et al., Stud. Surf. Sci. and Catal., 76, pages 105–144 (1993), which is herein incorporated by reference. In another embodiment, one or more binders are combined with one or more other non-limiting examples of alumina materials such as aluminum oxyhydroxide, γ-alumina, boehmite, diaspore, and transitional aluminas such as α-alumina, β-alumina, γ-alumina, δ-alumina, ε-alumina, κ-alumina, and ρ-alumina, aluminum trihydroxide, such as gibbsite, bayerite, nordstrandite, doyelite, and mixtures thereof.

In another embodiment, the binders are alumina sols, predominantly comprising aluminum oxide, optionally including some silicon. In yet another embodiment, the binders are peptized alumina made by treating alumina hydrates such as pseudobohemite, with an acid, preferably an acid that does not contain a halogen, to prepare sols or aluminum ion solutions. Non-limiting examples of commercially available colloidal alumina sols include Nalco 8676 available from Nalco Chemical Co., Naperville, Ill., and Nyacol available from The PQ Corporation, Valley Forge, Pa.

The molecular sieve synthesized above, in a preferred embodiment, is combined with one or more matrix material(s). Matrix materials are typically effective in reducing overall catalyst cost, act as thermal sinks assisting in shielding heat from the catalyst composition for example during regeneration, densifying the catalyst composition, increasing catalyst strength such as crush strength and attrition resistance, and to control the rate of conversion in a particular process.

Non-limiting examples of matrix materials include one or more of: rare earth metals, metal oxides including titania, zirconia, magnesia, thoria, beryllia, quartz, silica or sols, and mixtures thereof, for example silica-magnesia, silica-zirconia, silica-titania, silica-alumina and silica-alumina-thoria. In an embodiment, matrix materials are natural clays such as those from the families of montmorillonite and kaolin. These natural clays include subbentonites and those kaolins known as, for example, Dixie, McNamee, Georgia and Florida clays. Non-limiting examples of other matrix materials include: haloysite, kaolinite, dickite, nacrite, or anauxite. In one embodiment, the matrix material, preferably any of the clays, are subjected to well known modification processes such as calcination and/or acid treatment and/or chemical treatment.

In one preferred embodiment, the matrix material is a clay or a clay-type composition, preferably the clay or clay-type composition having a low iron or titania content, and most preferably the matrix material is kaolin. Kaolin has been found to form a pumpable, high solid content slurry, it has a low fresh surface area, and it packs together easily due to its platelet structure. A preferred average particle size of the matrix material, most preferably kaolin, is from about 0.1 $\mu$m to about 0.6 $\mu$m with a D90 particle size distribution of less than about 1 $\mu$m.

In one embodiment, the binder, the molecular sieve and the matrix material are combined in the presence of a liquid to form a molecular sieve catalyst composition, where the amount of binder is from about 2% by weight to about 30% by weight, preferably from about 5% by weight to about 20% by weight, and more preferably from about 7% by weight to about 15% by weight, based on the total weight of the binder, the molecular sieve and matrix material, excluding the liquid (after calcination).

In another embodiment, the weight ratio of the binder to the matrix material used in the formation of the molecular sieve catalyst composition is from 0:1 to 1:15, preferably 1:15 to 1:5, more preferably 1:10 to 1:4, and most preferably 1:6 to 1:5. It has been found that a higher sieve content, lower matrix content, increases the molecular sieve catalyst composition performance, however, lower sieve content, higher matrix material, improves the attrition resistance of the composition.

Upon combining the molecular sieve and the matrix material, optionally with a binder, in a liquid to form a slurry, mixing, preferably rigorous mixing is needed to produce a substantially homogeneous mixture containing the molecular sieve. Non-limiting examples of suitable liquids include one or a combination of water, alcohol, ketones, aldehydes, and/or esters. The most preferred liquid is water. In one embodiment, the slurry is colloid-milled for a period of time sufficient to produce the desired slurry texture, sub-particle size, and/or sub-particle size distribution.

The molecular sieve and matrix material, and the optional binder, are in the same or different liquid, and are combined in any order, together, simultaneously, sequentially, or a combination thereof. In the preferred embodiment, the same liquid, preferably water is used. The molecular sieve, matrix material, and optional binder, are combined in a liquid as solids, substantially dry or in a dried form, or as slurries, together or separately. If solids are added together as dry or substantially dried solids, it is preferable to add a limited and/or controlled amount of liquid.

In one embodiment, the slurry of the molecular sieve, binder and matrix materials is mixed or milled to achieve a sufficiently uniform slurry of sub-particles of the molecular sieve catalyst composition that is then fed to a forming unit that produces the molecular sieve catalyst composition. In a preferred embodiment, the forming unit is spray dryer. Typically, the forming unit is maintained at a temperature sufficient to remove most of the liquid from the slurry, and from the resulting molecular sieve catalyst composition. The resulting catalyst composition when formed in this way takes the form of microspheres.

When a spray drier is used as the forming unit, typically, the slurry of the molecular sieve and matrix material, and optionally a binder, is co-fed to the spray drying volume with a drying gas with an average inlet temperature ranging from 200° C. to 550° C., and a combined outlet temperature ranging from 100° C. to about 225° C. In an embodiment, the average diameter of the spray dried formed catalyst composition is from about 40 $\mu$m to about 300 $\mu$m, preferably from about 50 $\mu$m to about 250 $\mu$m, more preferably from about 50 $\mu$m to about 200 $\mu$m, and most preferably from about 65 $\mu$m to about 90 $\mu$m.

During spray drying, the slurry is passed through a nozzle distributing the slurry into small droplets, resembling an aerosol spray into a drying chamber. Atomization is achieved by forcing the slurry through a single nozzle or multiple nozzles with a pressure drop in the range of from 100 psia to 1000 psia (690 kPaa to 6895 kPaa). In another embodiment, the slurry is co-fed through a single nozzle or multiple nozzles along with an atomization fluid such as air, steam, flue gas, or any other suitable gas.

In yet another embodiment, the slurry described above is directed to the perimeter of a spinning wheel that distributes the slurry into small droplets, the size of which is controlled by many factors including slurry viscosity, surface tension, flow rate, pressure, and temperature of the slurry, the shape and dimension of the nozzle(s), or the spinning rate of the wheel. These droplets are then dried in a co-current or counter-current flow of air passing through a spray drier to form a substantially dried or dried molecular sieve catalyst composition, more specifically a molecular sieve in powder form.

Generally, the size of the powder is controlled to some extent by the solids content of the slurry. However, control of the size of the catalyst composition and its spherical characteristics are controllable by varying the slurry feed properties and conditions of atomization.

Other methods for forming a molecular sieve catalyst composition are described in U.S. patent application Ser. No. 09/617,714 filed Jul. 17, 2000 (spray drying using a recycled molecular sieve catalyst composition), which is herein incorporated by reference.

In another embodiment, the formulated molecular sieve catalyst composition contains from about 1% to about 99%, more preferably from about 5% to about 90%, and most preferably from about 10% to about 80%, by weight of the molecular sieve based on the total weight of the molecular sieve catalyst composition.

In another embodiment, the weight percent of binder in or on the spray dried molecular sieve catalyst composition based on the total weight of the binder, molecular sieve, and matrix material is from about 2% by weight to about 30% by weight, preferably from about 5% by weight to about 20% by weight, and more preferably from about 7% by weight to about 15% by weight.

Once the molecular sieve catalyst composition is formed in a substantially dry or dried state, to further harden and/or activate the formed catalyst composition, a heat treatment such as calcination, at an elevated temperature is usually performed. A conventional calcination environment is air that typically includes a small amount of water vapor. Typical calcination temperatures are in the range from about 400° C. to about 1,000° C., preferably from about 500° C. to about 800° C., and most preferably from about 550° C. to about 700° C., preferably in a calcination environment such as air, nitrogen, helium, flue gas (combustion product lean in oxygen), or any combination thereof.

In one embodiment, calcination of the formulated molecular sieve catalyst composition is carried out in any number of well known devices including rotary calciners, fluid bed calciners, batch ovens, and the like. Calcination time is typically dependent on the degree of hardening of the molecular sieve catalyst composition and the temperature ranges from about 15 minutes to about 2 hours.

In a preferred embodiment, the molecular sieve catalyst composition is heated in nitrogen at a temperature of from about 600° C. to about 700° C. Heating is carried out for a period of time typically from 30 minutes to 15 hours, preferably from 1 hour to about 10 hours, more preferably from about 1 hour to about 5 hours, and most preferably from about 2 hours to about 4 hours.

Other methods for activating a molecular sieve catalyst composition, in particular where the molecular sieve is a reaction product of the combination of a silicon-, phosphorous-, and aluminum-sources, a templating agent, and a polymeric base, more particularly a silicoaluminophosphate catalyst composition (SAPO) are described in, for example, U.S. Pat. No. 5,185,310 (heating molecular sieve of gel alumina and water to 450° C.), PCT WO 00/75072 published Dec. 14, 2000 (heating to leave an amount of template), and U.S. application Ser. No. 09/558,774 filed Apr. 26, 2000 (rejuvenation of molecular sieve), which are all herein fully incorporated by reference.

The process for converting a feedstock, especially a feedstock containing one or more oxygenates, in the presence of a molecular sieve catalyst composition according to the invention, is carried out in a reaction process in a reactor, where the process is a fixed bed process, a fluidized bed process, preferably a continuous fluidized bed process, and most preferably a continuous high velocity fluidized bed process.

The reaction processes can take place in a variety of catalytic reactors such as hybrid reactors that have a dense bed or fixed bed zones and/or fast fluidized bed reaction zones coupled together, circulating fluidized bed reactors, riser reactors, and the like. Suitable conventional reactor types are described in for example U.S. Pat. No. 4,076,796, U.S. Pat. No. 6,287,522 (dual riser), and *Fluidization Engineering*, D. Kunii and O. Levenspiel, Robert E. Krieger Publishing Company, New York, N.Y. 1977, which are all herein fully incorporated by reference.

The preferred reactor types are riser reactors generally described in *Riser Reactor, Fluidization and Fluid-Particle Systems*, pages 48 to 59, F. A. Zenz and D. F. Othrner, Reinhold Publishing Corporation, New York, 1960, and U.S. Pat. No. 6,166,282 (fast-fluidized bed reactor), and U.S. patent application Ser. No. 09/564,613 filed May 4, 2000 (multiple riser reactor), which are all herein fully incorporated by reference.

In the preferred embodiment, a fluidized bed process or high velocity fluidized bed process includes a reactor system, a regeneration system and a recovery system.

The reactor system preferably is a fluid bed reactor system having a first reaction zone within one or more riser reactor(s) and a second reaction zone within at least one disengaging vessel, preferably comprising one or more cyclones. In one embodiment, the one or more riser reactor(s) and disengaging vessel is contained within a single reactor vessel. Fresh feedstock, preferably containing one or more oxygenates, optionally with one or more diluent(s), is fed to the one or more riser reactor(s) in which a zeolite or zeolite-type molecular sieve catalyst composition or coked version thereof is introduced. In one embodiment, the molecular sieve catalyst composition or coked version thereof is contacted with a liquid or gas, or combination thereof, prior to being introduced to the riser reactor(s), preferably the liquid is water or methanol, and the gas is an inert gas such as nitrogen.

In an embodiment, the amount of liquid feedstock fed separately or jointly with a vapor feedstock, to a reactor system is in the range of from 0.1 weight percent to about 85 weight percent, preferably from about 1 weight percent to about 75 weight percent, more preferably from about 5 weight percent to about 65 weight percent based on the total weight of the feedstock including any diluent contained therein. The liquid and vapor feedstocks are preferably of similar composition, or contain varying proportions of the same or different feedstock with the same or different diluent.

Oxygenate to Olefins Process

In a preferred embodiment of the process of the invention, the feedstock contains one or more oxygenates, more specifically, one or more organic compound(s) containing at least one oxygen atom. In the most preferred embodiment of the process of invention, the oxygenate in the feedstock is one or more alcohol(s), preferably aliphatic alcohol(s) where the aliphatic moiety of the alcohol(s) has from 1 to 20 carbon atoms, preferably from 1 to 10 carbon atoms, and most preferably from 1 to 4 carbon atoms. The alcohols useful as feedstock in the process of the invention include lower straight and branched chain aliphatic alcohols and their unsaturated counterparts.

Non-limiting examples of oxygenates include methanol, ethanol, n-propanol, isopropanol, methyl ethyl ether, dimethyl ether, diethyl ether, di-isopropyl ether, formaldehyde, dimethyl carbonate, dimethyl ketone, acetic acid, and mixtures thereof.

In the most preferred embodiment, the feedstock is selected from one or more of methanol, ethanol, dimethyl ether, diethyl ether or a combination thereof, more preferably methanol and dimethyl ether, and most preferably methanol.

The various feedstocks discussed above, particularly a feedstock containing an oxygenate, more particularly a feedstock containing an alcohol, is converted primarily into one or more olefin(s). The olefin(s) or olefin monomer(s) produced from the feedstock typically have from 2 to 30 carbon atoms, preferably 2 to 8 carbon atoms, more preferably 2 to 6 carbon atoms, still more preferably 2 to 4 carbons atoms, and most preferably ethylene and/or propylene.

Non-limiting examples of olefin monomer(s) include ethylene, propylene, butene-1, pentene-1,4-methyl-pentene-1, hexene-1, octene-1 and decene-1, preferably ethylene, propylene, butene-1, pentene-1, 4-methyl-pentene-1, hexene-1, octene-1 and isomers thereof. Other olefin monomer(s) include unsaturated monomers, diolefins having 4 to 18 carbon atoms, conjugated or nonconjugated dienes, polyenes, vinyl monomers and cyclic olefins.

In the most preferred embodiment, the feedstock, preferably of one or more oxygenates, is converted in the presence of a molecular sieve catalyst composition into olefin(s) having 2 to 6 carbons atoms, preferably 2 to 4 carbon atoms. Most preferably, the olefin(s), alone or in combination, are converted from a feedstock containing an oxygenate, preferably an alcohol, most preferably methanol, to the preferred olefin(s) ethylene and/or propylene.

There are many processes used to convert feedstock into olefin(s) including various cracking processes such as steam cracking, thermal regenerative cracking, fluidized bed cracking, fluid catalytic cracking, deep catalytic cracking, and visbreaking.

The most preferred process is generally referred to as methanol-to-olefins (MTO). In a MTO process, typically an oxygenated feedstock, most preferably a methanol containing feedstock, is converted in the presence of a molecular sieve catalyst composition into one or more olefin(s), preferably and predominantly, ethylene and/or propylene, often referred to as light olefin(s).

In one embodiment of the process for conversion of a feedstock, preferably a feedstock containing one or more oxygenates, the amount of olefin(s) produced based on the total weight of hydrocarbon produced is greater than 50 weight percent, preferably greater than 60 weight percent, more preferably greater than 70 weight percent, and most preferably greater than 85 weight percent.

Increasing the selectivity of preferred hydrocarbon products such as ethylene and/or propylene from the conversion of an oxygenate using a molecular sieve catalyst composition is described in U.S. Pat. No. 6,137,022 (linear velocity), and PCT WO 00/74848 published Dec. 14, 2000 (methanol uptake index of at least 0.13), which are all herein fully incorporated by reference.

The feedstock, in one embodiment, contains one or more diluent(s), typically used to reduce the concentration of the feedstock, and are generally non-reactive to the feedstock or molecular sieve catalyst composition. Non-limiting examples of diluents include helium, argon, nitrogen, carbon monoxide, carbon dioxide, water, essentially non-reactive paraffins (especially alkanes such as methane, ethane, and propane), essentially non-reactive aromatic compounds, and mixtures thereof. The most preferred diluents are water and nitrogen, with water being particularly preferred.

The diluent, water, is used either in a liquid or a vapor form, or a combination thereof. The diluent is either added directly to a feedstock entering into a reactor or added directly into a reactor, or added with a molecular sieve catalyst composition. In one embodiment, the amount of diluent in the feedstock is in the range of from about 1 to about 99 mole percent based on the total number of moles of the feedstock and diluent, preferably from about 1 to 80 mole percent, more preferably from about 5 to about 50, most preferably from about 5 to about 25. In one embodiment, other hydrocarbons are added to a feedstock either directly or indirectly, and include olefin(s), paraffin(s), aromatic(s) (see for example U.S. Pat. No. 4,677,242, addition of aromatics) or mixtures thereof, preferably propylene, butylene, pentylene, and other hydrocarbons having 4 or more carbon atoms, or mixtures thereof.

The process for converting a feedstock, especially a feedstock containing one or more oxygenates, in the presence of a molecular sieve catalyst composition of the invention, is carried out in a reaction process in a reactor, where the process is a fixed bed process, a fluidized bed process, preferably a continuous fluidized bed process, and most preferably a continuous high velocity fluidized bed process.

The reaction processes can take place in a variety of catalytic reactors such as hybrid reactors that have a dense bed or fixed bed zones and/or fast fluidized bed reaction zones coupled together, circulating fluidized bed reactors, riser reactors, and the like. Suitable conventional reactor types are described in for example U.S. Pat. No. 4,076,796, U.S. Pat. No. 6,287,522 (dual riser), and *Fluidization Engineering*, D. Kunii and O. Levenspiel, Robert E. Krieger Publishing Company, New York, N.Y. 1977, which are all herein fully incorporated by reference.

The preferred reactor type are riser reactors generally described in *Riser Reactor, Fluidization and Fluid-Particle Systems*, pages 48 to 59, F. A. Zenz and D. F. Othmer, Reinhold Publishing Corporation, New York, 1960, and U.S. Pat. No. 6,166,282 (fast-fluidized bed reactor), and U.S. patent application Ser. No. 09/564,613 filed May 4, 2000 (multiple riser reactor), which are all herein fully incorporated by reference.

In the preferred embodiment, a fluidized bed process or high velocity fluidized bed process includes a reactor system, a regeneration system and a recovery system.

The reactor system preferably is a fluid bed reactor system having a first reaction zone within one or more riser reactor(s) and a second reaction zone within at least one disengaging vessel, preferably comprising one or more cyclones. In one embodiment, the one or more riser reactor(s) and disengaging vessel is contained within a single reactor vessel. Fresh feedstock, preferably containing one or more oxygenates, optionally with one or more diluent(s), is fed to the one or more riser reactor(s) in which a zeolite or zeolite-type molecular sieve catalyst composition or coked version thereof is introduced. In one embodiment, the molecular sieve catalyst composition or coked version thereof is contacted with a liquid or gas, or combination thereof, prior to being introduced to the riser reactor(s), preferably the liquid is water or methanol, and the gas is an inert gas such as nitrogen.

In an embodiment, the amount of liquid feedstock, which is processed by the present invention to provide liquids of reduced at least partial non-volatiles impurities, is fed separately or jointly with a vapor feedstock, to a reactor system in the range of from about 0 weight percent to about 85 weight percent, preferably from about 1 weight percent to about 75 weight percent, more preferably from about 5 weight percent to about 65 weight percent, say, from about 0 weight percent to about 10 weight percent, based on the total weight of the feedstock including any diluent contained therein. The liquid and vapor feedstocks are preferably of similar composition, or contain varying proportions of the same or different feedstock with the same or different diluent.

Treatment of the oxygenate-containing feedstock prior to its introduction to the oxygenate to olefins conversion reactor may be required to remove non-volatile contaminants. Moreover, it is advantageous to control the temperature within the reactor by controlling heat input to the feed in accordance with the present invention. This aspect of oxygenate to olefin conversion processes relates to the present invention and is discussed in greater detail below, in a section titled "Treatment of Oxygenate-Containing Feed."

The feedstock entering the reactor system is preferably converted, partially or fully, in the first reactor zone into a gaseous effluent that enters the disengaging vessel along with a coked molecular sieve catalyst composition. In the preferred embodiment, cyclone(s) within the disengaging vessel are designed to separate the molecular sieve catalyst composition, preferably a coked molecular sieve catalyst composition, from the gaseous effluent containing one or more olefin(s) within the disengaging zone. Cyclones are preferred, however, gravity effects within the disengaging vessel will also separate the catalyst compositions from the gaseous effluent. Other methods for separating the catalyst compositions from the gaseous effluent include the use of plates, caps, elbows, and the like.

In one embodiment of the disengaging system, the disengaging system includes a disengaging vessel, typically a lower portion of the disengaging vessel is a stripping zone. In the stripping zone the coked molecular sieve catalyst composition is contacted with a gas, preferably one or a combination of steam, methane, carbon dioxide, carbon monoxide, hydrogen, or an inert gas such as argon, preferably steam, to recover adsorbed hydrocarbons from the coked molecular sieve catalyst composition that is then introduced to the regeneration system. In another embodiment, the stripping zone is in a separate vessel from the disengaging vessel and the gas is passed at a gas hourly superficial velocity (GHSV) of from 1 $hr^{-1}$ to about 20,000 $hr^{-1}$ based on the volume of gas to volume of coked molecular sieve catalyst composition, preferably at an elevated temperature from 250° C. to about 750° C., preferably from about 350° C. to 650° C., over the coked molecular sieve catalyst composition.

The conversion temperature employed in the conversion process, specifically within the reactor system, is in the range of from about 200° C. to about 1000° C., preferably from about 250° C. to about 800° C., more preferably from about 250° C. to about 750° C., yet more preferably from about 300° C. to about 650° C., yet even more preferably from about 350° C. to about 600° C. most preferably from about 350° C. to about 550° C.

The conversion pressure employed in the conversion process, specifically within the reactor system, varies over a wide range including autogenous pressure. The conversion pressure is based on the partial pressure of the feedstock exclusive of any diluent therein. Typically the conversion pressure employed in the process is in the range of from about 0.1 kPaa to about 5 MPaa, preferably from about 5 kPaa to about 1 MPaa, and most preferably from about 20 kPaa to about 500 kPaa.

The weight hourly space velocity (WHSV), particularly in a process for converting a feedstock containing one or more oxygenates in the presence of a molecular sieve catalyst composition within a reaction zone, is defined as the total weight of the feedstock excluding any diluents to the reaction zone per hour per weight of molecular sieve in the molecular sieve catalyst composition in the reaction zone. The WHSV is maintained at a level sufficient to keep the catalyst composition in a fluidized state within a reactor.

Typically, the WHSV ranges from about 1 $hr^{-1}$ to about 5000 $hr^{-1}$, preferably from about 2 $hr^{-1}$ to about 3000 $hr^{-1}$, more preferably from about 5 $hr^{-1}$ to about 1500 $hr^{-1}$, and most preferably from about 10 $hr^{-1}$ to about 1000 $hr^{-1}$. In one preferred embodiment, the WHSV is greater than 20 $hr^{-1}$, preferably the WHSV for conversion of a feedstock containing methanol and dimethyl ether is in the range of from about 20 $hr^{-1}$ to about 300 $hr^{-1}$.

The superficial gas velocity (SGV) of the feedstock including diluent and reaction products within the reactor system is preferably sufficient to fluidize the molecular sieve catalyst composition within a reaction zone in the reactor. The SGV in the process, particularly within the reactor system, more particularly within the riser reactor(s), is at least 0.1 meter per second (m/sec), preferably greater than 0.5 m/sec, more preferably greater than 1 m/sec, even more preferably greater than 2 m/sec, yet even more preferably greater than 3 m/sec, and most preferably greater than 4 m/sec, e.g., greater than about 15 m/sec. See for example U.S. patent application Ser. No. 09/708,753 filed Nov. 8, 2000, which is herein incorporated by reference.

In one preferred embodiment of the process for converting an oxygenate to olefin(s) using a silicoaluminophosphate molecular sieve catalyst composition, the process is operated at a WHSV of at least 20 $hr^{-1}$ and a Temperature Corrected Normalized Methane Selectivity (TCNMS) of less than 0.016, preferably less than or equal to 0.01. See for example U.S. Pat. No. 5,952,538, which is herein fully incorporated by reference.

In another embodiment of the process for converting an oxygenate such as methanol to one or more olefin(s) using a molecular sieve catalyst composition, the WHSV is from 0.01 $hr^{-1}$ to about 100 $hr^{-1}$, at a temperature of from about 350° C. to 550° C., and silica to $Me_2O_3$ (Me is selected from group 13 (IIIA), groups 8, 9 and 10 (VIII) elements) from the Periodic Table of Elements), and a molar ratio of from 300 to 2500. See for example EP-0 642 485 B1, which is herein fully incorporated by reference.

Other processes for converting an oxygenate such as methanol to one or more olefin(s) using a molecular sieve catalyst composition are described in PCT WO 01/23500 published Apr. 5, 2001 (propane reduction at an average catalyst feedstock exposure of at least 1.0), which is herein incorporated by reference.

The coked molecular sieve catalyst composition is withdrawn from the disengaging vessel, preferably by one or more cyclones(s), and introduced to the regeneration system. The regeneration system comprises a regenerator where the coked catalyst composition is contacted with a regeneration medium, preferably a gas containing oxygen, under general regeneration conditions of temperature, pressure and residence time.

Non-limiting examples of the regeneration medium include one or more of oxygen, $O_3$, $SO_3$, $N_2O$, NO, $NO_2$, $N_2O_5$, air, air diluted with nitrogen or carbon dioxide, oxygen and water (U.S. Pat. No. 6,245,703), carbon monoxide and/or hydrogen. The regeneration conditions are those capable of burning coke from the coked catalyst composition, preferably to a level less than 0.5 weight percent based on the total weight of the coked molecular sieve catalyst composition entering the regeneration system. The coked molecular sieve catalyst composition withdrawn from the regenerator forms a regenerated molecular sieve catalyst composition.

The regeneration temperature is in the range of from about 200° C. to about 1500° C., preferably from about 300° C. to about 1000° C., more preferably from about 450° C. to about 750° C., and most preferably from about 550° C. to 700° C. The regeneration is in the range of from about 10 psia (68 kPaa) to about 500 psia (3448 kPaa), preferably from about 15 psia (103 kPaa) to about 250 psia (1724 kPaa), and more preferably from about 20 psia (138 kPaa) to about 150 psia (1034 kPaa). Typically, the pressure is less than about 60 psia (414 kPaa).

The preferred residence time of the molecular sieve catalyst composition in the regenerator is in the range of from about one minute to several hours, most preferably about one minute to 100 minutes, and the preferred volume of oxygen in the flue gas is in the range of from about 0.01 mole percent to about 5 mole percent based on the total volume of the gas.

In one embodiment, regeneration promoters, typically metal containing compounds such as platinum, palladium and the like, are added to the regenerator directly, or indirectly, for example with the coked catalyst composition. Also, in another embodiment, a fresh molecular sieve catalyst composition is added to the regenerator containing a regeneration medium of oxygen and water as described in U.S. Pat. No. 6,245,703, which is herein fully incorporated by reference.

In an embodiment, a portion of the coked molecular sieve catalyst composition from the regenerator is returned directly to the one or more riser reactor(s), or indirectly, by pre-contacting with the feedstock, or contacting with fresh molecular sieve catalyst composition, or contacting with a regenerated molecular sieve catalyst composition or a cooled regenerated molecular sieve catalyst composition described below.

The burning of coke is an exothermic reaction, and in an embodiment, the temperature within the regeneration system is controlled by various techniques in the art including feeding a cooled gas to the regenerator vessel, operated either in a batch, continuous, or semi-continuous mode, or a combination thereof. A preferred technique involves withdrawing the regenerated molecular sieve catalyst composition from the regeneration system and passing the regenerated molecular sieve catalyst composition through a catalyst cooler that forms a cooled regenerated molecular sieve catalyst composition. The catalyst cooler, in an embodiment, is a heat exchanger that is located either internal or external to the regeneration system.

In one embodiment, the cooler regenerated molecular sieve catalyst composition is returned to the regenerator in a continuous cycle, alternatively, (see U.S. patent application Ser. No. 09/587,766 filed Jun. 6, 2000) a portion of the cooled regenerated molecular sieve catalyst composition is returned to the regenerator vessel in a continuous cycle, and another portion of the cooled molecular sieve regenerated molecular sieve catalyst composition is returned to the riser reactor(s), directly or indirectly, or a portion of the regenerated molecular sieve catalyst composition or cooled regenerated molecular sieve catalyst composition is contacted with by-products within the gaseous effluent (PCT WO 00/49106 published Aug. 24, 2000), which are all herein fully incorporated by reference. In another embodiment, a regenerated molecular sieve catalyst composition contacted with an alcohol, preferably ethanol, 1-propnaol, 1-butanol or mixture thereof, is introduced to the reactor system, as described in U.S. patent application Ser. No. 09/785,122 filed Feb. 16, 2001, which is herein fully incorporated by reference.

Other methods for operating a regeneration system are disclosed in U.S. Pat. No. 6,290,916 (controlling moisture), which is herein fully incorporated by reference.

The regenerated molecular sieve catalyst composition withdrawn from the regeneration system, preferably from the catalyst cooler, is combined with a fresh molecular sieve catalyst composition and/or re-circulated molecular sieve catalyst composition and/or feedstock and/or fresh gas or liquids, and returned to the riser reactor(s). In another embodiment, the regenerated molecular sieve catalyst composition withdrawn from the regeneration system is returned to the riser reactor(s) directly, optionally after passing through a catalyst cooler. In one embodiment, a carrier, such as an inert gas, feedstock vapor, steam or the like, semi-continuously or continuously, facilitates the introduction of the regenerated molecular sieve catalyst composition to the reactor system, preferably to the one or more riser reactor(s).

In one embodiment, the optimum level of coke on the molecular sieve catalyst composition in the reaction zone is maintained by controlling the flow of the regenerated molecular sieve catalyst composition or cooled regenerated molecular sieve catalyst composition from the regeneration system to the reactor system. There are many techniques for controlling the flow of a molecular sieve catalyst composition described in Michael Louge, *Experimental Techniques, Circulating Fluidized Beds*, Grace, Avidan and Knowlton, eds., Blackie, 1997 (336–337), which is herein incorporated by reference. This is referred to as the complete regeneration mode. In another embodiment, the optimum level of coke on the molecular sieve catalyst composition in the reaction zone is maintained by controlling the flow rate of the oxygen-containing gas flow to the regenerator. This is referred to as the partial regeneration mode.

Coke levels on the molecular sieve catalyst composition are measured by withdrawing from the conversion process the molecular sieve catalyst composition at a point in the process and determining its carbon content. Typical levels of coke on the molecular sieve catalyst composition after regeneration are less than about 15 weight, say, less than about 2 weight percent, with levels of coke ranging from 0.01 weight percent to about 15 weight percent, preferably from about 0.05 weight percent to about 10 weight percent, based on the total weight of the molecular sieve and not the total weight of the molecular sieve catalyst composition.

In one embodiment, the molecular sieve catalyst composition in the reaction zone contains in the range of from about 1 to 50 weight percent, preferably from about 2 to 30 weight percent, more preferably from about 2 to about 20 weight percent, and most preferably from about 2 to about 10 weight percent coke or carbonaceous deposit based on the total weight of the mixture of molecular sieve catalyst compositions. See for example U.S. Pat. No. 6,023,005, which is herein fully incorporated by reference. It is recognized that the molecular sieve catalyst composition in the reaction zone is made up of a mixture of regenerated catalyst and catalyst that has ranging levels of carbonaceous deposits. The measured level of carbonaceous deposits thus represents an average of the levels an individual catalyst particle.

The gaseous effluent is withdrawn from the disengaging system and is passed through a recovery system. There are many well-known recovery systems, techniques and sequences that are useful in separating olefin(s) and purifying olefin(s) from the gaseous effluent. Recovery systems generally comprise one or more or a combination of various separation, fractionation and/or distillation towers, columns, splitters, or trains, for reaction systems such as ethylbenzene manufacture (U.S. Pat. No. 5,476,978) and other derivative processes such as aldehydes, ketones and ester manufacture (U.S. Pat. No. 5,675,041), and other associated equipment for example various condensers, heat exchangers, refrigeration systems or chill trains, compressors, knock-out drums or pots, pumps, and the like.

Non-limiting examples of these towers, columns, splitters or trains used alone or in combination include one or more of a demethanizer, preferably a high temperature demethanizer, a deethanizer, a depropanizer, preferably a wet depropanizer, a wash tower often referred to as a caustic wash tower and/or quench tower, absorbers, adsorbers, membranes, ethylene (C2) splitter, propylene (C3) splitter, butene (C4) splitter, and the like.

Various recovery systems useful for recovering predominately olefin(s), preferably prime or light olefin(s) such as ethylene, propylene and/or butene are described in U.S. Pat.

No. 5,960,643 (secondary rich ethylene stream), U.S. Pat. Nos. 5,019,143, 5,452,581 and 5,082,481 (membrane separations), U.S. Pat. No. 5,672,197 (pressure dependent adsorbents), U.S. Pat. No. 6,069,288 (hydrogen removal), U.S. Pat. No. 5,904,880 (recovered methanol to hydrogen and carbon dioxide in one step), U.S. Pat. No. 5,927,063 (recovered methanol to gas turbine power plant), and U.S. Pat. No. 6,121,504 (direct product quench), U.S. Pat. No. 6,121,503 (high purity olefins without superfractionation), and U.S. Pat. No. 6,293,998 (pressure swing adsorption), which are all herein fully incorporated by reference.

Generally accompanying most recovery systems is the production, generation or accumulation of additional products, by-products and/or contaminants along with the preferred prime products. The preferred prime products, the light olefins, such as ethylene and propylene, are typically purified for use in derivative manufacturing processes such as polymerization processes. Therefore, in the most preferred embodiment of the recovery system, the recovery system also includes a purification system. For example, the light olefin(s) produced particularly in a MTO process are passed through a purification system that removes low levels of by-products or contaminants.

Non-limiting examples of contaminants and by-products include generally polar compounds such as water, alcohols, carboxylic acids, ethers, carbon oxides, sulfur compounds such as hydrogen sulfide, carbonyl sulfides and mercaptans, ammonia and other nitrogen compounds, arsine, phosphine and chlorides. Other contaminants or by-products include hydrogen and hydrocarbons such as acetylene, methyl acetylene, propadiene, butadiene and butyne.

Other recovery systems that include purification systems, for example for the purification of olefin(s), are described in *Kirk-Othmer Encyclopedia of Chemical Technology*, 4th Edition, Volume 9, John Wiley & Sons, 1996, pages 249–271 and 894–899, which is herein incorporated by reference. Purification systems are also described in for example, U.S. Pat. No. 6,271,428 (purification of a diolefin hydrocarbon stream), U.S. Pat. No. 6,293,999 (separating propylene from propane), and U.S. patent application Ser. No. 09/689,363 filed Oct. 20, 2000 (purge stream using hydrating catalyst), which is herein incorporated by reference.

The present invention solves the current needs in the art by providing a method for converting a feed including an oxygenate to a product including a light olefin. The method of the present invention is conducted in a reactor apparatus. As used herein, the term "reactor apparatus" refers to an apparatus which includes at least a place in which an oxygenate to olefin conversion reaction takes place. As further used herein, the term "reaction zone" refers to the portion of a reactor apparatus in which the oxygenate to olefin conversion reaction takes place and is used synonymously with the term "reactor." Desirably, the reactor apparatus includes a reaction zone, an inlet zone and a disengaging zone. The "inlet zone" is the portion of the reactor apparatus into which feed and catalyst are introduced. The "reaction zone" is the portion of the reactor apparatus in which the feed is contacted with the catalyst under conditions effective to convert the oxygenate portion of the feed into a light olefin product. The "disengaging zone" is the portion of the reactor apparatus in which the catalyst and any additional solids in the reactor are separated from the products. Typically, the reaction zone is positioned between the inlet zone and the disengaging zone.

A preferred embodiment of a reactor system for the present invention is a circulating fluid bed reactor with continuous regeneration, similar to a modern fluid catalytic cracker. Fixed beds are not practical for the process because oxygenate to olefin conversion is a highly exothermic process which requires several stages with intercoolers or other cooling devices. The reaction also results in a high pressure drop due to the production of low pressure, low density gas.

Because the catalyst must be regenerated frequently, the reactor should allow easy removal of a portion of the catalyst to a regenerator, where the catalyst is subjected to a regeneration medium, preferably a gas comprising oxygen, most preferably air, to burn off coke from the catalyst, which restores the catalyst activity. The conditions of temperature, oxygen partial pressure, and residence time in the regenerator should be selected to achieve a coke content on regenerated catalyst of no greater than 10 carbon atoms per acid site of the molecular sieve in the catalyst, or the formulated catalyst itself. At least a portion of the regenerated catalyst should be returned to the reactor.

Treatment of Oxygenate-containing Feed

The present invention provides for increased efficiency in the removal of impurities/contaminants in the form of non-volatiles from a feed stream as well as increased performance in maintaining efficient temperature and pressure of the oxygenate feed.

For present purposes, "non-volatiles" are defined as materials which have negligible vapor pressure at the conditions necessary to prepare feed for the oxygenates to olefin conversion process. Typically, these conditions include temperatures ranging from about 32° to about 500° F., and pressures ranging from about 20 psia to about 150 psia, preferably temperatures ranging from about 200° to about 400° F., and pressures ranging from about 20 psia to about 100 psia, say from about 50 psia to about 95 psia. These materials are thus neither sublimable nor boilable at oxygenate to olefins feed conditions.

In one embodiment, non-volatile materials include inorganic metals, salts, acids and bases, dirt, clay, sand, and mixtures and alloys of inorganic materials, e.g., catalyst fines. Such non-volatile materials can include organic compounds that exhibit a negligible vapor pressure at the conditions necessary to prepare a feed for the oxygenate to olefins conversion process. Examples of non-volatile organic compounds include asphaltenes, polymers, tars, coal, waxes, heavy oils, silicone oils and silicon polymers. Most of the non-volatile materials are either solids or viscous liquids at ambient conditions. In addition to materials that exhibit negligible vapor pressure at the conditions necessary to prepare feed for the oxygenate to olefins conversion process, deleterious components that boil at temperatures greater than the oxygenate feed may also be present in the oxygenate-containing feed. Such components include crude oil, heavy naphthas, distillates and other petroleum fractions or blend stocks, as well as processed petroleum products, chemicals produced from petroleum products, lubricating oils, hydraulic oils, oil additives, as well as non-carbon based chemicals and inorganic chemicals including, but not limited to, those containing halogens. Many of the deleterious boilable components exhibit low vapor pressures at the conditions necessary to prepare feed for the oxygenates to olefin process and hence are either essentially non-volatile or partially non-volatile materials. Such non-volatile or partially non-volatile materials not only reduce or eliminate catalyst performance but can deposit on internal surfaces of the oxygenate to olefin conversion reactor as well as apparatus situated downstream of the conversion reactor, e.g. the product recovery train. Many of these at least partially non-volatile contaminants in oxygenate containing feeds are introduced from residual materials present in logistics systems such as ships, tanks, and pipelines employed in the storage and transportation of these feeds.

In one aspect of the present invention, the term "non-volatiles" describes materials having essentially no or very low vapor pressure at the temperature and pressure necessary to prepare feed for the oxygenate to olefins process. Although most materials having vapor pressures less than the oxygenate feed will partition between the liquid and the vapor phases, for present purposes, "partial non-volatiles" are defined as materials having a normal boiling point (at one atmosphere pressure) at least 200° F. higher than the dominant oxygenate component in the feed. For example, methanol has a normal boiling point of about 148° F., and dodecane has a normal boiling point of about 421° F. and benzene has a normal boiling point of about 176° F. For the purposes of this invention dodecane is defined as a partial non-volatile whereas benzene is defined as volatile. It will be recognized by those skilled in the art that detailed calculations or experiments are possible to estimate the approximate separation of all materials in the oxygenate feed that have measurable vapor pressures. These calculations can be used to estimate the efficiency of the invention.

The disengaging drum receives an oxygenated feed from at least one feed pre-heater and provides an effluent stream to an oxygenate to olefin (OTO) reactor(s). Installed in a recycle loop for the drum is a heat exchange means comprising at least one heat exchanger, external to the vapor-liquid disengaging drum. In one embodiment, the heat exchanger means comprises a plurality of heat exchangers. The heat exchangers may be installed in parallel relative to each other. In a particular embodiment, at least two heat exchangers are installed in parallel to each other in the recycle loop.

The specific heat exchanger employed can be any heat exchanger suitable for its purpose in the invention. For purposes of the present invention a heat exchanger is defined as a means for transferring heat from a heat source, such as heat exchange fluid to a heated material, in this case the liquid effluent from the vapor-liquid disengaging drum, through a heat transferring medium located between the heat source and the heated material, such as metal. Heat transfer is thereby accomplished without physically contacting the heat source with the heated material.

Suitable heat exchangers for use herein can be selected from horizontal or vertical shell and tube exchangers configured for partial vaporization. In one embodiment, at least one exchanger comprises a circulating partial vaporizer where the circulation of the effluent liquid is either induced by at least one of i) mechanically pumping the effluent through the exchanger or ii) a thermosyphon where weight or static head of the effluent liquid is greater than the weight or static head of the heat exchanged and partially vaporized effluent returning to the drum, thus inducing circulation through the exchanger. The circulating partial vaporizer can be situated externally to the vapor-liquid disengaging drum. Partial vaporizers utilizing mechanical pumps for circulation are preferred where the source of heat for the exchanger is either remote or in a location that does not permit the use of a thermosyphon.

Partial vaporizers can be configured to vaporize from about 5 to about 95 vol % of the circulating fluid, say, from about 20 to about 40 vol %, e.g., from about 30 to about 40 vol % of the circulating fluid. This level of vaporization mostly prevents the deposition of non-volatiles and partial non-volatiles in the heat exchanger.

In an embodiment of the invention, heat is supplied to the heat exchanging means, e.g., a partial vaporizer, for exchange to the liquid oxygenate-containing stream from the vapor-liquid disengaging drum from at least one of externally supplied steam, water from a quench operation, e.g., water used to quench an oxygenates to olefin conversion effluent stream (with attendant quenched products in the water), and the oxygenates to olefin conversion effluent itself. Operating plural heat exchangers located in parallel to one another provides desired flexibility. Flexibility in controlling heat exchange may further be provided by using more than one type of heat source to the heat exchanger means, e.g., providing each heat exchanger with a different type of heat source.

The heat exchanging means at least partially vaporizes the oxygenate-containing feed and delivers the at least partially vaporized feed to the vapor-liquid disengaging drum for separation into a vapor that exits the drum overhead and liquid that combines with the preheated oxygenate feed entering the drum. The combined liquid in the drum circulates to the heat exchanging means and is at least partially vaporized again. The vapor-liquid disengaging drum approximates a theoretical single fractionation stage. The non-volatiles and partially non-volatiles mostly remain in the liquid concentrating to a level determined by the concentration of non-volatiles and partially non-volatiles in the feed and the percent by weight of the total feed withdrawn from the drum as liquid blowdown. The overall percentage by weight of the fresh oxygenate-containing feed (excluding recycle streams) vaporized in the drum is 100 wt % minus the percentage by weight of blowdown. In one embodiment, the total feed withdrawn as blowdown can range from about 1 to about 20 wt %, say, from about 1 to about 10 wt %, e.g., from about 1 to about 5 wt %. The amount of non-volatiles in the vapor leaving the drum is related to the amount of unseparated liquid mist carried overhead with the vapor from the drum. The amount of non-volatiles in the mist is inversely proportional to the weight percentage of blowdown. Thus a measure of control is exercisable over the amount of non-volatiles carried overhead with the vapor by increasing or decreasing the percentage of the total feed to the blowdown. The approximate concentration of non-volatiles in the oxygenate liquid in the drum is subject to calculation. At some elevated concentration level in the liquid, the non-volatiles and partially non-volatiles begin to separate as a solid phase in the drum. The blowdown rate or weight percentage of fresh feed must be maintained at a sufficient level to avoid accumulations of a solid phase in the drum. Inasmuch as the properties of non-volatiles or partial non-volatiles can be expected to vary, a drum liquid analysis can be used to establish the blowdown weight percentage. A partial analysis of non-volatiles can be obtained using a conductivity probe, wherein ion concentration in an oxygenate liquid phase is related to conductivity. In one embodiment, the conductivity probe is installed online and may be used to control the blowdown rate.

Because the oxygenate feedstock normally is stored at ambient temperatures before use in the conversion process, the feedstock has to be heated to a higher temperature with a much higher heat content suitable for contacting the oxygenate conversion catalyst. The heat content of the feedstock can be used as a factor for varying the temperature at which the oxygenate to olefin conversion reactor is operated.

It is preferable to increase the heat content and/or the temperature of the feedstock through from one to about three intermediate stages, with each stage having a successively higher heat content. Many different streams in the oxygenate conversion process may be suitable sources for providing the necessary heat to increase heat contents. These streams include those derived from the heavy product fraction from the quench tower and the streams from the fractionator separating quench medium from other components. It should be pointed out that a stream may have a higher heat content after a heat exchange even though it has a lower temperature, primarily resulting from pressure changes and/or phase changes, such as vaporization of a liquid as may occur in an oxygenates to olefins conversion process. In one embodiment of the invention, the reactor feed temperature is further increased in a fourth stage of heat exchange on the vapor feed to the reactor. Steam can be used as a source of heat in this stage of heat exchange.

In accordance with one embodiment of the present invention the preheated feedstream is then fed into at least one disengaging drum capable of maintaining proper pressure and separating impurities out of the oxygenate feed. Preferably only a single disengaging drum is employed inasmuch as a single feed vapor-liquid disengaging drum with multiple heat exchanger inputs is the least complex means to approach a single theoretical stage of fractionation sufficient to reject substantially all non-heavy hydrocarbon non-volatiles and many of the heavy hydrocarbons as well. The oxygenate feed then needs be at least partially vaporized and contacted in a suitable oxygenate conversion reactor with the selected molecular sieve catalyst under process conditions effective to produce the desired olefins at an acceptable conversion level with desired selectivity.

The OTO catalyst is also susceptible to poisons in the oxygenate-containing feed that include metals, salts and heavy hydrocarbons. These poisons can incapacitate a catalyst, either temporarily or permanently, and therefore it is desirable to remove them completely from the oxygenate-containing feed to the OTO reactor.

In one embodiment of the invention, after contacting the oxygenate feedstock with the oxygenate conversion catalyst present in the OTO reactor, the oxygenate conversion reaction product effluent comprising olefin products is quenched directly by contacting a suitable quench medium in a quench tower. The compounds in the effluent stream that are gaseous under the quenching conditions are separated from the quench tower as a light product fraction for olefin product recovery and purification. The light product fraction comprises light olefins, dimethyl ether, methane, CO, $CO_2$, ethane, propane, and other minor components such as water and unreacted oxygenate feedstock. The compounds in the effluent stream that are liquid under quenching conditions, are separated from the quench tower as a heavy product fraction for heat recovery, and possible division into several fractions and separation of the quench medium. The heavy product fraction comprises byproduct water, a portion of the unreacted oxygenate feedstock (except those oxygenates that are gases under quenching conditions), a small portion of the oxygenate conversion byproducts, particularly heavy hydrocarbons ($C_5^+$), and usually the bulk of the quench medium. Further details of such reactions may be found in U.S. Pat. No. 6,121,504.

In an embodiment of the present invention wherein more than one vapor/liquid disengaging drum is utilized, the primary or controlling drum has an independent source of steam, whereas the secondary drum or drums typically do not. Typically, the secondary drums are maintained under at least the same pressure as the primary drum. The treated oxygenate feed vapor from the vapor/liquid disengaging drums is passed to the oxygenate to olefins reactors through the primary drum.

Referring to the FIGURE, one aspect of the invention and a number of the preferred embodiments are shown. Prior to the present invention it has been exceedingly difficult to produce a clean effluent feed that had been vaporized while still maintained at a proper pressure and temperature.

In an embodiment of the invention, the feed vaporization process for an OTO reactor(s) begins with an oxygenate-containing feed 2 which contains impurities which, if not at least partially removed, can deleteriously deposit on internal surfaces throughout the apparatus of the process. One or more pumps 6 can be used to maintain or facilitate flow of the feed. The oxygenate-containing feed 2 is heated by one or more feed preheaters 8, 10 and 12 which may be arranged serially and/or in parallel, prior to being fed into a vapor-liquid disengaging drum 14 via vapor-liquid disengaging drum inlet 16.

The vapor-liquid disengaging drum 14 is the primary location where non-volatiles present in the oxygenate-containing feed are separated from volatiles, e.g., materials that are distillable and/or sublimable under the conditions used to prepare OTO feeds. The disengaging drum 14 contains a boilable fluid medium such as an oxygenate compound which is used as a heat sink to control the temperature within the vapor-liquid disengaging drum. The drum is operated so as to maintain the oxygenate feed at a predetermined temperature and pressure. The temperature and pressure levels are maintained sufficient to provide an at least partially vaporized effluent stream (or phase) and an at least partially liquid stream (or phase).

The at least partially vaporized effluent stream is passed through drum outlet 18, optionally through an optional wash column demister 20 comprising packing and demister screens 22 and 24 and having an upper inlet 26 for a wash column demister liquid oxygenate reflux 28 and eventually fed as vapor via line 30 into an OTO reactor and/or directed via valve 32 to an upper inlet 34 of condenser 36 having a bottoms outlet 36 through which liquid condensed oxygenate is passed to pump 38 for transmission to condenser recycle inlet 40, to wash column demister 20 as a demister wash column wash via line 28, and/or to an OTO reactor via line 42. Thus in one embodiment of the invention a liquid effluent is fed into an OTO reactor. This liquid feed should be free of non-volatiles and kept close to its vapor point. The liquid feed is used to control the temperature in the OTO reactor and the proportion of vapor to liquid feed used is dependent on the OTO reactor conditions as described above. The wash column demister 20 will further remove any entrenched non-volatiles.

The at least partially liquid stream (or phase) from the vapor-liquid disengaging drum is passed through a vapor-liquid disengaging drum liquid stream outlet 44 via line 46 to a heat exchanging means. The heat exchanging means can comprise a plurality of partial vaporizers 48, 50 and 52, respectively, installed in parallel inlet lines 54, 56 and 58, respectively. Heat is thus added to the at least partially liquid stream and a heated at least partially vapor stream removed from the heat exchangers via lines 60, 62 and 64, thence through line 66 to a second inlet 68 to said vapor-liquid disengaging drum 14. Heat is supplied to the partial vaporizers 48, 50 and 52, via hot oxygenate to olefins reactor effluent 49, steam 51, and/or hot quench liquid 53 resulting from quenching oxygenate to olefins reactor effluent, e.g., using water quench. Heat input to the heat exchangers is controlled so as to provide a heat exchanged vapor phase oxygenate-containing stream of sufficient heat content as vaporized feed via drum outlet 18 for OTO reactor requirements.

In one aspect of the invention, the vapor phase is removed through drum outlet 18. The vapor phase is free of non-volatiles except for liquid phase mist carried with the vapor phase through outlet 18. The majority of the non-volatiles accumulate in the liquid phase and can be removed from the disengaging drum as blowdown via blowdown outlet 70. These non-volatiles may be disposed of in a variety of useful manners known in the art. In one embodiment volatiles trapped in the blowdown are removed by conveying blowdown via pump 72 to the top of condensate stripper 74 via line 75. Alternatively, the blowdown can be conveyed to the condensate stripper through intermediate condensate stripper inlet 76, particularly in those instances where an alternate source of reflux is made available to the top of said condensate stripper as discussed below. The condensate stripper is heated in a condensate stripper bottoms heat exchanger 78 wherein heat is added to bottoms taken from condensate stripper outlet 80 via line 82. The heated bottoms are returned to the condensate stripper via line 84. The bottoms, which contain water, heavy hydrocarbons and non-volatiles, may be removed via line 86 to a disposal or recycle system, which may include a water treatment plant. In one embodiment, the solids and heavy hydrocarbons from the blowdown can be directed to heavy oil removal and separation systems included with the aforementioned quench systems used to treat oxygenate to olefins reactor effluent.

Condensate containing oxygenates, e.g., methanol and water, such as that provided by quenching an oxygenate to olefins reactor effluent as discussed above can be separately added to condensate stripper 74 via intermediate condensate stripper inlet 86. Condensate stripper overhead is removed from the condensate stripper by line 88 and recycled to vapor-liquid disengaging drum through vapor-liquid disengaging drum inlet 90. In one embodiment, the overhead from line 88 is directed through line 92 controlled by valve 94 to a condensate stripper overhead condenser drum 96, which separates out non-condensables from condensable liquids. This condensate stripper overhead condenser drum is separate from said vapor-liquid disengaging drum 14. A vapor-containing stream is taken off the condensate stripper overhead condenser drum 96 through line 98 and from which a liquid-containing stream is taken via line 100 and directed by reflux pump 102 to i) the top of condensate stripper 74 via line 104 and/or ii) an oxygenate to olefins reactor inlet via lines 105 and 42. Regulating the flow of these liquid-containing streams via lines 105 and/or 42 can be used to control temperature in the oxygenate to olefins reactor. These liquid-containing streams that contain extremely low levels of at least partial non-volatiles as contaminants are thus well-suited as feeds to the reactor. The vapor-containing stream can be subsequently flared or utilized as fuel. In an alternate embodiment, at least a portion of the condensate stripper overhead is directed via line 89 as vaporized effluent 30 into an OTO reactor. This is particularly suited where reflux to the condensate stripper 74 is provided by an alternate oxygenate-containing stream such as blowdown from the vapor-liquid disengaging drum 70.

In a particular embodiment of the present invention, an oxygenates to olefins reactor effluent, e.g., 49 is taken via line 106 to a reactor effluent quench unit 108 whose bottoms can be directed to condensate stripper 74 via line 110 and intermediate condensate stripper inlet 86. Quench unit overhead containing olefins is taken via line 112 to initial olefin recovery unit 114 and thence via line 116 to a product recovery wash system 118, e.g., a column, to which water or oxygenate-containing wash is fed via line 120 to remove water and/or oxygenates. Typically, an oxygenate-containing wash can be derived from oxygenate feed, condensate, boiler feed water, process water or product oxygenates, as well as other suitable sources. The oxygenates in the wash extract may be recovered and purified as feed for the oxygenates to olefins reactor. Wash extract is removed via line 124 to quench tower 108 or condensate stripper 74. Washed overhead is taken via line 126 to additional olefins recovery unit 128.

Persons of ordinary skill in the art will recognize that many modifications may be made to the present invention without departing from the spirit and scope of the present invention. The embodiment described herein is meant to be illustrative only and should not be taken as limiting the invention, which is defined by the following claims.

What is claimed is:

1. A process for converting oxygenates to olefins which comprises:

contacting a vaporized oxygenate-containing feed with a catalyst comprising a molecular sieve under conditions sufficient to provide an oxygenates to olefin effluent stream, and further comprising:

providing said vaporized oxygenate-containing feed by:

a) passing an initial oxygenate-containing feed having an initial heat content through at least one feed preheater under conditions sufficient to provide a feed of increased heat content;

b) directing said feed of increased heat content to at least one vapor-liquid disengaging drum;

c) providing conditions within said vapor-liquid disengaging drum sufficient to provide a vaporized oxygenate-containing stream and a liquid oxygenate-containing stream further comprising at least partial non-volatiles, wherein the boiling point of said oxygenates of said oxygenate-containing feed within said drum is controlled by varying the total pressure within the vapor-liquid disengaging drum so as to impart sufficient heat content to said vaporized oxygenate-containing stream, such that said contacting of the vaporized oxygenate-containing feed with said catalyst provides said effluent stream which comprises a super-heated gas phase comprising olefins, unreacted oxygenate, and water at a temperature above that of said initial oxygenate-containing feed;

d) heat exchanging said liquid oxygenate-containing stream by passage through at least one heat exchanger, external to said vapor-liquid disengaging drum, wherein heat is added to said liquid oxygenate-containing stream from said oxygenates to olefin effluent stream to provide a heat exchanged, at least partially vapor phase, oxygenate-containing stream; and e) directing said heat exchanged stream to said vapor-liquid disengaging drum.

2. The process of claim 1 wherein said at least one heat exchanger comprises a circulating partial vaporizer where said passage through the exchanger is induced by at least one of i) mechanically pumping said liquid oxygenate-containing stream through the heat exchanger and ii) thermosyphon circulation where the weight or density multiplied by height of the liquid oxygenate-containing stream minus total frictional losses being greater than the weight or density multiplied by height of the heat exchanged at least partially vapor phase, oxygenate-containing stream, drives said circulation.

3. The process of claim 2 wherein said at least one heat exchanger comprises a plurality of heat exchangers arranged in parallel.

4. The process of claim 3 wherein at least one of said heat exchangers derives its heat from steam.

5. The process of claim 4 wherein at least one of said heat exchangers derives heat from water used to quench said oxygenates to olefin effluent stream.

6. The process of claim 4 wherein said steam provides from about 10% to about 70% of said heat added to said liquid oxygenate-containing stream.

7. The process of claim 2 wherein said heat exchanging is carried out to effect vaporization ranging from about 5 to about 95% of said liquid oxygenate-containing stream per pass through said circulating partial vaporizer.

8. The process of claim 2 wherein said heat exchanging is carried out to effect vaporization ranging from about 20 to about 40% of said liquid oxygenate-containing stream per pass through said circulating partial vaporizer.

9. The process of claim 1 wherein said liquid oxygenate-containing stream in said drum accumulates a desired proportion of said at least partial non-volatiles to provide an at least partial non-volatiles-rich, oxygenate-containing stream which is removable as blowdown.

10. The process of claim 9 wherein said at least partial non-volatiles-rich, oxygenate containing stream accumulates non-volatiles to a steady state level of from about 5 to about 100 times the level of non-volatiles in said initial oxygenate-containing feed, wherein liquid blowdown is removed from said vapor-liquid disengaging drum at a rate ranging from about 1% to about 20% by weight of said feed directed to said drum.

11. The process of claim 9 which comprises:

passing said blowdown as a feed to a condensate stripper to provide an at least partial non-volatiles-rich bottoms stream and an oxygenates-rich overhead.

12. The process of claim 11 wherein said oxygenates-rich overhead is recycled to said vapor-liquid disengaging drum.

13. The process of claim 11 wherein said oxygenates-rich overhead is recycled to a vapor-liquid disengaging drum and at least a portion of said blowdown is directed to a condensate stripper.

14. The process of claim 11 wherein said oxygenates-rich overhead is directed to a vapor-liquid disengaging drum at least a portion of whose condensed liquid is directed to an oxygenates to olefin reactor as a liquid oxygenates-containing feed reduced in said at least partial non-volatiles.

15. The process of claim 1 which further comprises:

passing said vaporized oxygenate-containing stream from said vapor-liquid disengaging drum to a demister which provides a demisted oxygenate-containing stream as overhead, reduced in said at least partial non-volatiles.

16. The process of claim 15 wherein said demister comprises a wash column.

17. The process of claim 16 wherein said wash column utilizes a liquid oxygenate-containing stream as wash liquid.

18. The process of claim 17 which further comprises directing at least some of said overhead from the demister to a condenser to provide a liquid oxygenate-containing bottoms stream.

19. The process of claim 18 wherein at least a portion of said bottoms stream is used as a feed to an oxygenates to olefin reactor.

20. The process of claim 18 wherein at least a portion of said bottoms stream is used as wash liquid in said demister.

21. The process of claim 1 wherein said at least one vapor-liquid disengaging drum is a single vapor-liquid disengaging drum.

22. The process of claim 1 wherein said oxygenate-containing feed comprises methanol.

23. The process of claim 21 wherein said vapor-liquid disengaging drum is maintained at a pressure ranging from about 20 to about 150 psia.

24. The process of claim 21 wherein said vapor-liquid disengaging drum is maintained at a pressure ranging from about 50 to about 95 psia.

* * * * *